US009173958B2

(12) United States Patent
Foote et al.

(10) Patent No.: US 9,173,958 B2
(45) Date of Patent: Nov. 3, 2015

(54) ANTIBODY BUFFERING OF A LIGAND IN VIVO

(75) Inventors: Jefferson Foote, Seattle, WA (US); Carol E. O'Hear, Seattle, WA (US)

(73) Assignee: Arrowsmith Technologies Corporation, Seattle, WA (US)

( * ) Notice: Subject to any disclaimer, the term of this patent is extended or adjusted under 35 U.S.C. 154(b) by 0 days.

(21) Appl. No.: 11/226,055

(22) Filed: Sep. 13, 2005

(65) Prior Publication Data
US 2006/0062778 A1 Mar. 23, 2006

Related U.S. Application Data

(60) Provisional application No. 60/609,803, filed on Sep. 13, 2004.

(51) Int. Cl.
*C07K 16/44* (2006.01)
*A61K 49/16* (2006.01)
*A61K 47/48* (2006.01)
*A61K 39/395* (2006.01)
*A61K 45/06* (2006.01)
*C07K 16/18* (2006.01)
*C07K 16/40* (2006.01)
*A61K 39/00* (2006.01)

(52) U.S. Cl.
CPC ..... *A61K 47/48376* (2013.01); *A61K 39/39583* (2013.01); *A61K 45/06* (2013.01); *C07K 16/18* (2013.01); *C07K 16/40* (2013.01); *C07K 16/44* (2013.01); *A61K 2039/505* (2013.01); *C07K 2317/92* (2013.01)

(58) Field of Classification Search
None
See application file for complete search history.

(56) References Cited

U.S. PATENT DOCUMENTS

| 2,623,071 | A | 12/1952 | Bowles | |
|---|---|---|---|---|
| 5,106,951 | A | 4/1992 | Morgan, Jr. et al. | 530/391.9 |
| 6,414,033 | B1 | 7/2002 | Sceusa | 514/648 |
| 6,881,557 | B2 | 4/2005 | Foote | 435/69.6 |
| 2002/0122810 | A1 | 9/2002 | Cubicciotti | 424/400 |

FOREIGN PATENT DOCUMENTS

| EP | 0409212 A2 | 1/1991 |
|---|---|---|
| WO | WO 94/04569 A1 | 3/1994 |
| WO | WO 01/20018 A2 | 3/2001 |
| WO | WO 2005/094881 A | 10/2005 |
| WO | WO 2006/051288 A2 | 5/2006 |

OTHER PUBLICATIONS

Kroll et al., Therapeutic Immunology 1:333-341, Dec. 1994.*
Tangri et al., Current Medicinal Chemistry, 9:2191-2199, Dec. 2002.*
Balsari et al. International Journal of Cancer 47:889-892, Apr. 1991.*
O'Hear and Foote, J Mol Biol, Sep. 16, 2006.*
Mihara et al., Immunology, 74:55-59, 1991.*
Finkelman et al., The Journal of Immunology, 151(3):1235-1244, 1993.*
Aspirin Monograph. Retrieved [online] on Mar. 26, 2010. Retrieved from: <http://www.medscape.com/druginfo/dosage?cid=med&drugid=1082&drugname=Aspirin+Oral&monotype=default>.*
Keiser et al., Nature, 462:175-182, Nov. 2009.*
Balsari et al., Int J Cancer, 47: 889-892, 1991.*
May et al., J Immunol, 151(6):3225-3236, Sep. 15, 1993.*
Finkelman et al., J Immunol, 151:1235-1244, 1993.*
Conlon et al., Biotechnol Ther., 1(1):31-41, 1989.*
Puri RK, Methods Mol Biol., 166:155-176, 2001.*
Agu, R. U. et al., "Intranasal Delivery of Recombinant Human Parathyroid Hormone [hPTH (1-34)], Teriparatide in Rats," *Endocrine Research*, 30(3):455-467, 2004.
Amit, A. G. et al., "Three-Dimensional Structure of an Antigen-Antibody Complex at 2.8 Å Resolution," *Science*, 233:474-753, Aug. 1986.
Anderson, J. H. et al., "Clinical Pharmacokinetic Advantages of New Drug Delivery Methods for the Treatment of Liver Tumours," *Clinical Pharmacokinetics*, 27(3):191-201, 1994.
Balthasar, J. P. and Fung, H-L., "Inverse Targeting of Peritoneal Tumors: Selective Alteration of the Disposition of Methotrexate through the Use of Anti-Methotrexate Antibodies and Antibody Fragments," *Journal of Pharmaceutical Sciences*, 85(10):1035-1043, Oct. 1996.
Balthasar, J. P. and Fung, H-L., "Utilization of Antidrug Antibody Fragments for the Optimization of Intraperitoneal Drug Therapy: Studies Using Digoxin as a Model Drug," *The Journal of Pharmacology and Experimental Therapeutics*, 268(2):734-739, 1994.
Begley, D. J., "Delivery of therapeutic agents to the central nervous system: the problems and the possibilities," *Pharmacology & Therapeutics*, 104:29-45, 2004.
Berek, C. et al., "Activation of memory and virgin B cell clones in hyperimmune animals," *Eur. J. Immunol.*, 17:1121-1129, 1987.
Bergsneider, M., "Evolving Concepts of Cerebrospinal Fluid Physiology," *Neurosurgery Clinics of North America*, 36(4):631-638, Oct. 2001.
Bialer, M., "Pharmacokinetic Evaluation of Sustained Release Formulations of Antiepileptic Drugs," *Clinical Pharmacokinetics*, 22(1):11-21, 1992.
Blasberg, R. G. et al., "Intrathecal Chemotherapy: Brain Tissue Profiles After Ventriculo-Cisternal Perfusion," *The Journal of Pharmacology and Experimental Therapeutics*, 195(1):73-83, 1975.
Castro, M. G. et al., "Current and future strategies for the treatment of malignant brain tumors," *Pharmacology & Therapeutics*, 98:71-108, 2003.
Cheng, J. et al., "Antitumor Activity of β-Cyclodextrin Polymer—Campthothecin Conjugates," *Molecular Pharmaceutics*, 1(3):183-193, Apr. 3, 2004.

(Continued)

Primary Examiner — Daniel E Kolker
Assistant Examiner — Stacey N MacFarlane
(74) Attorney, Agent, or Firm — Wilmer Cutler Pickering Hale and Dorr LLP

(57) ABSTRACT

Compositions and methods are provided in embodiments directed to maintaining a desired concentration range of one or more drugs in a subject, and in particular embodiments to maintaining a desired drug concentration in a body compartment in a subject, based on the surprising discovery that antibodies persist in solution in body compartments such that antibody-antigen equilibrium principles can counteract drug clearance mechanisms. One or more antibodies are selected that have a dissociation constant $K_D$ that is similar to the desired drug concentration, wherein $K_D$ is independent of the affinity of the drug for a specific drug target (receptor) in the subject.

21 Claims, 13 Drawing Sheets

(56) References Cited

OTHER PUBLICATIONS

Colby, D. W. et al., "Engineering Antibody Affinity by Yeast Surface Display," *Methods in Enzymology*, 388:348-358, 2004.
Das, D. and Suresh, M. R., "Producing Bispecific and Bifunctional Antibodies," *Methods in Molecular Medicine*, 109:329-345, 2005.
Dash, A. K. and Cudworth, G. C. II., "Therapeutic Applications of Implantable Drug Delivery Systems," *Journal of Pharmacological and Toxicological Methods*, 40(1):1-12, 1998.
Dedrick, R. L. et al., "Pharmacokinetic Rationale for Peritoneal Drug Administration in the Treatment of Ovarian Cancer," *Cancer Treatment Reports*, 62(1):1-11, Jan. 1978.
Drakeman, D. L. et al., "Bispecific antibodies for the treatment of tumours and infectious diseases," *Exp. Opin. Invest. Drugs*, 6(9):1169-1178, 1997.
Foote, J. and Winter, G., "Antibody Framework Residues Affecting the Conformation of the Hypervariable Loops," *Journal of Molecular Biology*, 224(1):487-499, 1992.
Gordon, K. B. et al., "Hand-Foot Syndrome Associated with Liposome-Encapsulated Doxorubicin Therapy," *Cancer*, 75(8):2169-2173, Apr. 15, 1995.
Goskonda, V. R. et al., "Novel Site-Specific Chemical Delivery System as a Potential Mydriatic Agent: Formation of Phenylephrine in the Iris-Ciliary Body from Phenylephrone Chemical Delivery Systems," *Journal of Pharmaceutical Sciences*, 90(1):12-22, Jan. 2001.
Goyal, P. et al., "Liposomal drug delivery systems—Clinical applications," *Acta Pharm.*, 55:1-25, 2005.
Griffiths, G. M. et al., "Somatic mutation and the maturation of immune response to 2-phenyl oxazolone," *Nature*, 312:271-275, Nov. 15, 1984.
Groothuis, D. R. and Levy, R. M., "The entry of antiviral and antiretroviral drugs into the central nervous system," *Journal of NeuroVirology*, 3:387-400, 1997.
Hanes, J. et al., "Ribosome display efficiently selects and evolves high-affinity antibodies in vitro from immune libraries," *PNAS, USA*, 95:14130-14135, Nov. 1998.
Holt, L. J. et al., "Domain antibodies: proteins for therapy," *Trends in Biotechnology*, 21(11):484-490, Nov. 2003.
Hopkins, K. and Kemshead, J. T., "Progress Review: Intrathecal and Intratumoral Injection of Radiolabelled Monoclonal Antibodies (MoAbs) for the Treatment of Central Nervous System (CNS) Malignancies," *Journal of Drug Targeting*, 1:175-183, 1993.
Huang, X. and Brazel, C. S., "On the importance and mechanisms of burst release in matrix-controlled drug delivery systems," *Journal of Controlled Release*, 73:121-136, 2001.
Hudson, P. J. and Kortt, A. A., "High avidity scFv multimers; diabodies and triabodies," *Journal of Immunological Methods*, 231:177-189, 1999.
Jaeckle, K. A. et al., "An open label trial of sustained-release cytarabine (DepoCyt™) for the Intrathecal treatment of solid tumor neoplastic meningitis," *Journal of Neouro-Oncology*, 57:231-239, 2002.
Kipriyanov, S. M., "Generation of Bispecific and Tandem Diabodies," *Methods in Molecular Biology*, 178:317-331, 2002.
Koch-Weser, J. and Sellers, E. M., "Medical Intelligence—Drug Therapy: Binding of Drugs to Serum Albumin (First of Two Parts)," *The New England Journal of Medicine*, 294(6):311-316, Feb. 5, 1976.
Koelemij, R. et al:, "Bispecific Antibodies in Cancer Therapy, from the Laboratory to the Clinic," *Journal of Immunotherapy*, 22(6):514-524, 1999.
Kremer, J. M. H. et al., "Drug Binding to Human Alpha-1-acid Glycoprotein in Health and Disease," *Pharmacological Reviews*, 40(1):1-47, Mar. 1988.
Langner, M. and Ugorski, M., "The Macromolecular Aggregate as a Drug Carrier," *Cellular & Molecular Biology Letters*, 5(4):433-400, 2000.
Lobo, E. D. et al., "Application of Pharmacokinetic—Pharmacodynamic Modeling to Predict the Kinetic and Dynamic Effects of Anti-Methotrexate Antibodies in Mice," *Journal of Pharmaceutical Sciences*, 92(8):1665-1676, Aug. 2003.
Lotem, M. et al., "Skin Toxic Effects of Polyethylene Glycol-Coated Liposomal Doxorubicin," *Arch. Dermatol.*, 136:1475-1480, Dec. 2000.
Lyass, O. et al., "Correlation of Toxicity with Pharmacokinetics of Pegylated Liposomal Doxorubicin (Doxil) in Metastatic Breast Carcinoma," *Cancer*, 89(5):1037-1047, Sep. 1, 2000.
Marvin, J. S. and Zhu, Z., "Recombinant approaches to IgG-like Bispecific antibodies," *Acta Pharmacologica Sinica*, 26(6):649-658, Jun. 2005.
McClay, E. F. and Howell, S. B., "Intraperitoneal Therapy in the Management of Patients with Ovarian Cancer," *Hematology/Oncology Clinics of N. America*, 6(4):915-926, Aug. 1992.
O'Hear, C. E. and Foote, J., "Antibody buffering of a ligand in vivo," *PNAS, USA*, 102(1):40-44, Jan. 4, 2005.
Oh, C. et al., "A Compartmental Model for the Ocular Pharmacokinetics of Cyclosporine in Rabbits," *Pharmaceutical Research*, 12(3):433-437, 1995.
Ohning, B. L., "Neonatal Pharmacodynamics—Basic Principles I: Drug Delivery," *Neonatal Network*, 14(2):7-12, Mar. 1995.
Ohning, B. L., "Neonatal Pharmacodynamics—Basic Principles II: Drug Action and Elimination," *Neonatal Network*, 14(2):15-19, Mar. 1995.
Olivier, J-C., "Drug Transport to Brain with Targeted Nanoparticles," *NeuroRx®: The Journal of the American Society for Experimental NeuroTherapeutics*, 2(1):108-119, Jan. 2005.
Peipp, M. and Valerius, T., "Bispecific antibodies targeting cancer cells," *Biochemical Society Transactions*, 30(4):507-511, 2002.
Pell, J. M. and James, S., "Immuno-enhancement and—inhibition of GH-releasing factor by site-directed anti peptide antibodies in vivo and in vitro," *Journal of Endocrinology*, 146(3):535-541, Sep. 1995.
Pettit, D. K. and Gombotz, W. R., "The development of site-specific drug-delivery systems for protein and peptide biopharmaceuticals," *Trends Biotechnol.*, 16:343-349, Aug. 1998.
Presta, L. G., "Engineering Antibodies for Therapy," *Current Pharmaceutical Biotechnology*, 3(3):237-256, 2002.
Rang, H.P. et al., (Eds.) Pharmacology, $5^{th}$ Edition, *Churchill Livingstone, London, 2003*, Chapter 2, "How drugs act: general principles," pp. 7-21.
Rehlaender, B. N. and Cho. M. J., "Antibodies as Carrier Proteins," *Pharmaceutical Research*, 15(11):1652-1656, 1998.
Saishin, Y. et al., "Periocular Injection of Microspheres Containing PKC412 Inhibits Choroidal Neovascularization in Porcine Model," *Investigative Ophthalmology & Visual Science*, 44(11):4989-4993, Nov. 2003.
Siegal, T. and Zylber-Katz, E., "Strategies for Increasing Drug Delivery to the Brain," *Clin. Pharmacokinet.*, 41(3):171-186, 2002.
Sood, A. and Panchagnula, R., "Design of controlled release delivery systems using a modified pharmacokinetic approach: a case study for drugs having a short elimination half-life and a narrow therapeutic index," *International Journal of Pharmaceutics*, 261:27-41, 2003.
Sparreboom, A. et al., "The (ir)relevance of plasma protein binding of anticancer drugs," *The Netherlands Journal of Medicine*, 59:196-207, 2001.
Stewart, C. E. H. et al., "Potentiation of Insulin-like Growth Factor-1 (IGF-1) Activity by an Antibody: Supportive Evidence for Enhancement of IGF-1 Bioavailability In Vivo by IGF Binding Proteins," *Endocrinology*, 133(3):1462-1465, 1993.
Inooka H. et al., "Ameliorating Agent for Stabilizing a Mammalian Endogenous Ligand in Blood, Comprises an Antibody having Affinity with a Mammalian Endogenous Ligand and Substantially Not Neutralizing the Same," *Derwent Publications Ltd.*, pp. 1-3, Oct. 2005.
Lobo E.D. et al., "Antibody Pharmacokinetics and Pharmacodynamics," *Journal of Pharmaceutical Sciences*, 93:2645-2648, Nov. 2004.
Mihara M. et al., "Murine Anti-Human IL-6 Monoclonal Antibody Prolongs the Half-Life in Circulating Blood and Thus Prolongs the Bioactivity of Human IL-6 in Mice," *Immunology* 74:55-59, May 1991.
O'Hear, "Antibody Buffering: A Novel Mechanism of Drug Delivery," *Dissertation Abstracts International*, 65(10):4999, Apr. 2005.
O'Hear et al., "Antibody Buffering in the Brain," *Journal of Molecular Biology*, 364:1003-1009, 2006.

(56) References Cited

OTHER PUBLICATIONS

O'Hear et al., "Antibody Buffering of Systematically-Administered Lysozyme," *Journal of Investigative Medicine, American Federation for Clinical Research*, 50(1):49A, 2002.

Pell J.M. et al., "Principles of Immunomodulation," *Livestock Production Science*, 42:123-133, 1995.

Were, et al., "Encapsulation of Nisin and Lysozyme in Liposomes Enhances Efficacy Against *Listeria monocytogenes*", Journal of Food Protection, 67(5):922-927, May 2004, 8 pages.

Loeffler, et al., "Phage Lytic Enzyme Cpl-1 as a Novel Antimicrobial for Pneumococcal Bacteremia", Infection and Immunity, 71(11):6199-6204, Nov. 2003, 6 pages.

Jado, et al., "Phage Lytic Enzymes as Therapy for Antibiotic-Resistant *Streptococcus pneumoniae* Infection in a Murine Sepsis Model", Journal of Antimicrobial Chemotherapy, 52:967-973, Nov. 12, 2003, 7 pages.

Srinivas, et al., "Controlled Release of Lysozyme from Succinylated Gelatin Microspheres", Journal of Biomaterials Science, 12(2):137-148, Apr. 2, 2012, 14 pages.

Du Vigneaud, et al., "Synthetic Penicillin", Science, 104(2706):431-433 and 450, Nov. 8, 1946, 5 pages.

Swann, "The Search for Synthetic Penicillin During World War II", The British Journal for the History of Science, vol. 16, Part 1, No. 52, pp. 154-190, Mar. 1983, 39 pages.

International Preliminary Report on Patentability issued in the International Application No. PCT/US2005/032911, filed Sep. 13, 2005, 13 pages.

International Search Report and Written opinion issued in the International Application No. PCT/US2005/032911, filed Sep. 13, 2005, 18 pages.

O'Hear, "Antibody Buffering: a Novel Mechanism of Drug Delivery," A dissertation, University of Washington, 154 pages, Sep. 14, 2004.

\* cited by examiner

ANTIBODY BUFFERING OF A LIGAND IN VIVO

CROSS-REFERENCE TO RELATED APPLICATION

This application claims the benefit under 35 U.S.C. §119 (e) of U.S. Provisional Patent Application No. 60/609,803 entitled "Antibody buffering of a ligand in vivo" and filed by Carol E. O'Hear and Jefferson Foote on Sep. 13, 2004, which provisional application is incorporated herein by reference in its entirety.

STATEMENT OF GOVERNMENT INTEREST

This invention was made with government support under Grant No. NIH T32 CA80416 awarded by the National Institutes of Health. The government may have certain rights in this invention.

BACKGROUND OF THE INVENTION

1. Field of the Invention

The present invention relates generally to the use of antibodies as biopharmacological buffers for regulating drug concentration, half-life, bioactivity and/or bioavailability. More specifically, invention embodiments as disclosed herein relate to regionally administering a drug and a specific anti-drug antibody, to treat a disease or disorder in a selected body compartment.

2. Description of the Related Art

Despite the fact that a vast number of diseases in humans and animals are characterized by adverse pathophysiological effects that are localized to particular sites, tissues or organs in an afflicted individual, the majority of therapeutic treatment regimens for such conditions involve systemic or global administration of a therapeutic drug, for example, via oral or intravenous routes. (See, e.g., Rang, H. P. et al. (Eds.), Pharmacology, 2003 Churchill Livingstone, New York, Ch. 7, pp. 91-105.) Consequently, pharmacologic or suprapharmacologic levels of a drug are often achieved in clinically irrelevant, inappropriate and/or undesirable anatomical locations within the recipient (including circulating plasma concentrations), as the by-product of efforts to attain a therapeutically effective level of such drug at a relatively restricted site. Drug clearance and degradation activities in the body often necessitate repeated administration of the drug, which can often lead to recurring wide fluctuations in the actual circulating drug concentration.

For instance, chemotherapy plays a significant role in the current treatment regime for young children with brain tumors because radiation often leads to developmental delay and neuroendocrine deficiencies in these patients (Zalutsky, 2004 Br. J. Canc. 90:1469). Tumors of the central nervous system (CNS) represent the second most frequent malignancy in children under the age of 15 years (Heideman et al., 1997 Cancer 80:497). Forty-five percent of these children will die of their disease, but not well recorded is the morbidity of the survivors, a result of the motor and intellectual deficits associated with the aggressive chemotherapeutic protocols currently used, as well as with the tumors themselves. Given that many brain-intrinsic neoplasms are characterized by relentless tumor cell infiltration of normal brain parenchyma, strategies for targeting therapeutic agents to tumors often feature drugs having diffusive properties, in order for them to reach invading tumor cell clusters that migrate along vascular clefts and axonal pathways (Merlo et al., 2003 Acta Neurochir. Suppl. 88:83).

Despite their widespread application, the use of chemotherapeutic agents in treatment of solid tumors involving the brain parenchyma has not been very successful (Castro et al., 2003 Pharmacol. Ther. 98:71). Tumors of the CNS are usually slow-growing, so treatment regimens with the cell cycle-inhibiting drugs currently available typically call for these agents to remain at an effective concentration for a lengthy period of time. Achieving this effective drug concentration at the tumor site for such time periods represents a major technical obstacle (Blasberg, 1975 J. Pharmacol. Exp. Ther. 195: 73). Further drawbacks to the use of chemotherapy are the development of chemoresistant cells, and inadequate drug delivery methods (Castro et al., 2003). Also troubling is that although anticancer drugs may kill tumor cells, useful dosage ranges for such drugs are limited by global drug toxicity to hematopoietic cells, leading to undesirable myelosuppression.

The problem of effective drug delivery to a restricted site, whether in the CNS or elsewhere, is compounded by a variety of factors such as drug absorption and stability in vivo (e.g., Bialer, 1992 Clin. Pharmacokinet. 22:11), physiological drug clearance and elimination mechanisms (e.g., Anderson et al., 1994 Clin. Pharmacokinet. 27:191), drug inactivation by binding to plasma proteins in the circulation and/or to proteins in interstitial fluids (e.g., Koch-Weser et al., 1976 N. Engl. J. Med. 294:311; Kremer et al., 1988 Pharmacol. Rev. 40:1; Sparreboom et al., 2001 Neth. J. Med. 59:196), and drug accessibility to specific drug target molecules in affected cells and tissues (e.g., Begley, 2004 Pharmacol. Therapeut. 104: 29). In particular, impediments to the effective delivery of a systemically administered drug to a restricted site arise as a result of physical, anatomical, pharmacokinetic and/or physiological barriers that separate a number of body compartments.

The CNS, for example, is rendered a discrete body compartment by the blood-brain barrier (BBB; e.g., Begley, 2004). As other examples, the eye, the joint capsule including the relatively avascular articular cartilage (e.g., WO 01/20018 and references cited therein), the pleural sac, the peritoneum and the pericardium represent additional body compartments into which effective, localized drug delivery can be problematic.

Multiple strategies have been devised in efforts to deliver effective amounts of therapeutic drugs to such body compartments using global administration such as oral or intravenous routes. These strategies include formulation of drugs for delivery as polymers, gels, microcarriers, liposomes, aggregates, affinity-targeted conjugates, inhalants, microspheres, viral vectors, iontophoresis agents, chemically modified derivatives, sustained release formulations, and other formats (e.g., Cheng et al., 2004 Mol. Pharm. 1:183; Goyal et al., 2005 Acta Pharm. 55:1; Agu et al., 2004 Endocr. Res. 30:455; Siashin et al., 2003 Invest. Ophthalmol. Vis. Sci. 44:4989; Goskonda et al., 2001 J. Pharm. Sci. 90:12; Pettit et al., 1998 Trends Biotechnol. 16:343; Groothuis et al., 1997 J. Neurovirol. 3:387; Langner et al., 200 Cell. Molec. Biol. Lett. 5:433; Ohning 1995 Neonatal Netw. 14:7; Ohning 1995 Neonatal Netw. 14:15; Sood et al., 2003 Int J. Pharmaceut. 261:27; Olivier, 2005 NeuroRx 2:108). With regard to specific delivery to a desired body compartment, however, these approaches are plagued by one or more shortcomings that include, for example, difficulties in achieving desired local drug levels, difficulties in maintaining desired local drug levels over time, non-specific passive diffusion and/or active transport of drug to undesired compartments, premature clearance and/or elimination of the drug, adverse collateral effects on adjacent tissues that result from drug delivery, inadequate accessibility of the compartment to drug, unsuitability of the active ingredient to the delivery modification, and other problems. (e.g., Baker, 1987 Controlled Release of Biologically Active Agents, John Wiley & Sons, NY; Dash et al., 1998 *J. Pharmacol. Toxicol. Meths.* 40:1; Huang et al., 2001 *J. Control Release* 73:121; Gordon et al., 1995 *Cancer* 75:2169; Lotem et al., 2000 *Arch. Dermatol.* 136:1475; Lyass et al., 2000 *Cancer* 89:1037.

In certain cases, alternative attempts to achieve specific and effective delivery of a therapeutic drug to a body compartment have involved direct injection of the drug to the afflicted area (Rang, H. P. et al. (Eds.), In Pharmacology, 2003, pp. 91-105; Begley, 2004 *Pharmacol. Therap.* 104:29; Anderson et al., 1994 *Clin. Pharmacokinet.* 27:191; Dedrick et al., 1978 *Canc. Treat. Rep.* 62:1; Clay et al., 1992 *Hematol. Oncol. Clin. N. Am.* 6:915; Oh et al., 1995 *Pharm. Res.* 12:433; Hopkins et al., 1993 *J. Drug Target* 1:175). Such approaches have, however, been plagued by issues of safety, efficacy, cost, convenience and other factors, and not all body compartments are amenable to multiple direct interventions over a therapeutic timeframe. For example, direct injection to the CNS is accompanied by risks associated with irreversible damage to CNS tissue and the potential for microbial infection associated with repeated access to a site, and the CNS as well as other compartments may only be directly accessible through skill- and labor-intensive surgical procedures. Additionally, therapeutic drugs administered directly to the CNS may not persist there, being released instead from the CNS to the general circulation as a consequence of the directional bulk flow of CNS interstitial fluid (e.g., Bergsneider 2001 *Neurosurg. Clin. N. Amer.* 12:631). As another example, cancer therapy involving direct intraperitoneal injection of an anti-cancer drug has resulted in leakage of significant and potentially toxic levels of the drug out of the peritoneal compartment and into the general circulation (e.g., Balthasar et al., 1994 *J. Pharmacol. Exp. Ther.* 268:734; Balthasar et al., 1996 *J. Pharm. Sci.* 85:1035; Lobo et al., 2003 *J. Pharm. Sci.* 92:1665).

Clearly there is a need for improved methods and compositions for administering and delivering drugs without repeated direct intervention, and in a manner that permits maintenance of a desired level of the drug in a selected body compartment. New approaches would also desirably avoid unwanted consequences of non-specific drug delivery, such as wide fluctuations in local drug concentrations or other clinically detrimental effects. The present invention fulfills such needs and offers other related advantages.

BRIEF SUMMARY OF THE INVENTION

According to certain embodiments of the present invention there is provided a method for maintaining a desired concentration range of one or more drugs in a subject, comprising administering to the subject simultaneously or sequentially and in either order (i) at least one dose of a drug and (ii) at least one antibody, or an antigen-binding fragment thereof, that specifically binds to the drug, wherein for the antibody an antibody dissociation constant, $K_D$, has a value that is substantially similar to the desired concentration of the drug, and wherein the antibody dissociation constant $K_D$ is independent of affinity of the drug for a specific drug target in the subject.

In another embodiment there is provided a method for maintaining a desired concentration range of one or more drugs in a body compartment in a subject, comprising administering to the body compartment simultaneously or sequentially and in either order (i) at least one dose of a drug and (ii) at least one antibody, or an antigen-binding fragment thereof, that specifically binds to the drug, wherein for said antibody an antibody dissociation constant, $K_D$, has a value that is substantially similar to the desired concentration of the drug, and wherein the antibody dissociation constant $K_D$ is independent of affinity of the drug for a specific drug target in the subject.

In certain further embodiments of the above described methods, the body compartment comprises a compartment that is selected from a central nervous system compartment, a pericardium, a pleural space, a retro-orbital compartment, an eye compartment, a joint capsule, a lymphoid compartment, a peritoneal compartment, an intranasal compartment, a lung compartment, and a genitourinary compartment. In certain such embodiments the body compartment comprises a central nervous system compartment. In certain further embodiments of the above described methods the body compartment comprises a central nervous system compartment and the step of administering comprises introduction of the drug intrathecally, intraventricularly, parenchymally, subdurally, subarachnoidally or epidurally.

In certain other further embodiments of the above described methods, the method comprises administering at least two doses of the drug. In other further embodiments the antibody and the drug are administered in approximately equimolar concentrations. In other further embodiments the antibody and the drug are administered at an antibody-to-drug molar ratio of at least 2:1. In other further embodiments the antibody is a monoclonal antibody, and in certain other further embodiments the antibody is a chimeric antibody or a humanized antibody. In certain other further embodiments the antigen-binding fragment is selected from a Fab fragment, a Fab' fragment, a $(Fab')_2$ fragment, an Fd fragment, an Fv fragment, an scFv, a dAb and a diabody.

In a distinct further embodiment of the above described methods, the step of administering comprises administering at least one dose of a first drug and at least one first antibody, or an antigen-binding fragment thereof, that specifically binds to the first drug; and administering at least one dose of a second drug and at least one second antibody, or an antigen-binding fragment thereof, that specifically binds to the second drug. In certain other further embodiments of the above described methods, the antibody, or antigen-binding fragment thereof, comprises a plurality of antibodies or antigen-binding fragments thereof, that specifically bind to the drug, wherein each of said antibodies has an antibody dissociation constant, $K_D$, that has a value that is substantially similar to a desired concentration that is within the desired concentration range of the drug.

In another embodiment the invention provides a method for maintaining a desired concentration range of a drug in a central nervous system compartment in a subject, comprising administering to the central nervous system compartment simultaneously or sequentially and in either order (i) at least one dose of the drug and (ii) an antibody, or an antigen-binding fragment thereof, that specifically binds to the drug, wherein for said antibody an antibody dissociation constant, $K_D$, has a value that is substantially similar to the desired concentration of the drug, and wherein the antibody dissociation constant $K_D$ is independent of affinity of the drug for a specific drug target in the subject. In certain further embodiments the subject has a central nervous system disease or disorder, which in certain still further embodiments is a neoplastic condition, a neurodegenerative disease, a vascular disease or an autoimmune disease. In one embodiment the subject has a neoplastic condition of the central nervous system. In a further embodiment the neoplastic condition is selected from glioma, astrocytoma, neurofibroma, neuroblastoma, lymphoma, a brain metastasis, and a tumor that is present in at least one of brain parenchyma, meninges, cranial nerve, pituitary gland, pineal gland, oligodendroglia, ependyma and choroid plexus.

Turning to another embodiment, there is provided a method for identifying an antibody that is capable of maintaining a desired concentration range of a drug in a body compartment in a subject, comprising determining a desired concentration range of a drug to be maintained in a body compartment in the subject; and preparing an antibody that specifically binds to the drug and that has an antibody dissociation constant, $K_D$, having a value that is substantially similar to the desired concentration of the drug to be maintained in the body compartment, and thereby identifying an antibody that is capable of maintaining the desired concentration range of the drug.

These and other aspects of the present invention will become apparent upon reference to the following detailed description. To this end, various references are set forth herein which describe in more detail certain background information, procedures, compounds and/or compositions, and are each hereby incorporated by reference as if set forth in their entirety.

BRIEF DESCRIPTION OF THE DRAWINGS

FIG. 5 depicts long term buffering of Ox by the anti-Ox antibody NQ11/7.12. To each rat in a group of five rats, Ox was administered with antibody (squares) at time 0. Ox was again administered without antibody at 24 hours (triangles) and at 48 hours (open circles). In another group of animals, Ox was administered with a non-specific antibody (D1.3, anti-hen egg white lysozyme) (filled circles).

FIG. 8 illustrates the half-life of ox and the free Ox concentration in plasma of rats when Ox was administered with anti-Ox antibodies that have different $K_d$s for Ox.

FIG. 10 illustrates analyses of $^{14}$C-lysozyme.

DETAILED DESCRIPTION OF THE INVENTION

Figure 1:
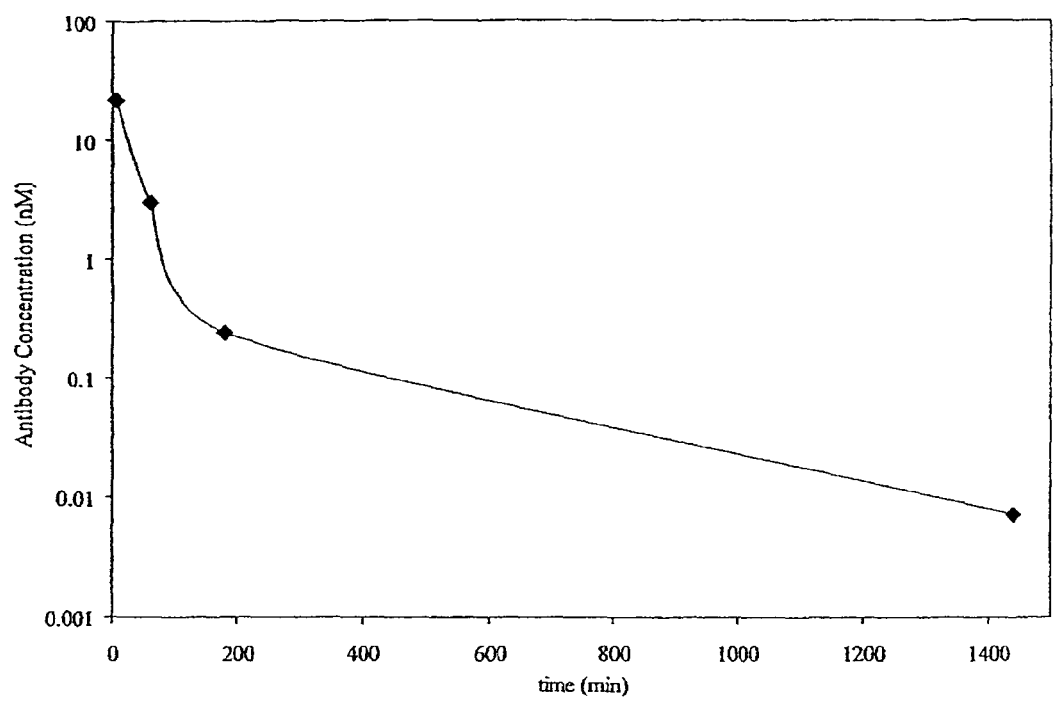
FIG. 1 illustrates elimination of the anti-Ox antibody NQ11/7.12 from the cisterna magna. Radioiodinated NQ11/7.12 was infused into the cisterna mangna; CSF samples were withdrawn at the times shown and counted to determine antibody concentration.

The present invention relates, in certain embodiments, to methods and compositions for maintaining a desired concentration range of a drug in a subject in vivo, by administering to the subject the drug and an antibody that specifically binds to the drug.

Antibody Buffering

As presently disclosed, these and related embodiments derive from the surprising observation that within a body compartment, the effective half-life of a drug can be prolonged, i.e., drug clearance can be retarded or delayed in a statistically significant manner, by the presence of anti-drug antibodies. Such antibodies thus mediate what is described herein as an "antibody buffering" effect, whereby an in vivo equilibrium distribution, between (i) a drug that is complexed with an antibody and (ii) unbound free drug, can be regulated as a function of antibody affinity properties, to obtain a desired concentration range of free, bioavailable drug.

Hence, and as an unexpected and useful function of the in vivo equilibrium dynamics of antibody-drug association and dissociation, appropriately selected anti-drug antibodies may be employed to maintain a drug concentration in a body compartment by releasing a subpopulation of bound drug molecules in the course of a perpetual re-equilibration process, as dissociated free drug molecules are eliminated by physiological clearance mechanisms and/or removed through interactions with specific drug targets (pharmacological receptors).

Suitable anti-drug antibodies may be selected that have an antibody dissociation constant, $K_D$, with a value that is substantially similar to the desired concentration of the drug in the body compartment, wherein $K_D$ is independent of the affinity of the drug for any specific drug target in the subject. As elaborated below, these and related embodiments as disclosed herein offer numerous advantages for therapeutic methods, including reduced frequency of drug administration, maintenance of predictable drug concentration ranges, reduced consumption and waste of drug products, reduced toxicity from excessive drug dosage, and other related advantages.

By way of background, all drugs are cleared from the body, in most cases by a first order process in which the amount of drug cleared per unit time is proportional to the amount of drug that is present. As also noted above, clinical dosing typically yields an initial drug level far higher than the threshold for efficacy, which level plummets as a consequence of first order clearance but may then be restored by administration of subsequent doses. The result is a recurring pattern of significant fluctuation in the in vivo drug concentration. By contrast, most modern drugs interact with a specific drug target (pharmacological receptor) that behaves as a saturable receptor for the drug in a cell, tissue or organ, which drug target may be a discrete or transient uni- or multi-molecular structure or a functional biological activity. At a drug concentration that is higher than the saturating concentration for the specific drug target, no further drug effects accrue and in fact undesirable effects may be manifest. Hence, typical fluctuations in drug concentration that result from clearance may lead to swings between suboptimal efficacy (at drug concentration lows) and adverse side-effects (at drug concentration highs).

Further by way of background, antibody-antigen interactions in solution are known to conform to well-established principals of chemical dynamics, which include the Law of Mass Action and the Law of Chemical Equilibrium (I. Pecht, 1982 in The Antigens, Vol. 6 (M. Sela, Ed.), Academic Press, NY, pp. 1-68; M. W. Steward, 1974, Immunochemistry, Chapman and Hall, London), and which permit characterization of an antibody according to the well known parameter referred to as the antibody dissociation constant. The antibody dissociation constant provides a quantitative indicator of the strength of antibody binding to antigen in terms of the relative ease with which an antibody-antigen complex may dissociate. In other words, the antibody dissociation constant may be viewed as an indicator of the relative concentrations of antibody and/or antigen that would be present for antibody-antigen complex formation to be favored, or for dissociation of such complexes into free antibody and free antigen to be favored.

Briefly, an antibody dissociation constant, $K_D$, may be determined for any particular antibody on the basis of the equilibrium distribution between the concentrations of free antibody [Ab], free antigen [Ag], and antibody-antigen complexes [AbAg], where $K_D=[Ab][Ag]/[AbAg]$ and has the physical dimension of concentration (e.g., molarity, M). $K_D$ can also be measured from the kinetic rate constants of AbAg complex formation ($k_{on}$) and complex dissociation ($k_{off}$) into free Ab and free Ag, whereby $K_D=k_{off}/k_{on}$. Alternatively, where all three components (free Ab, free Ag and complexed AbAg) cannot be measured simultaneously, $K_D$ can be determined by determining the antibody concentration at which half of the antigen concentration is complexed with antibody, at which concentration $K_D=[Ab]$.

As noted above, drugs typically exert their biological and/or pharmacological effects through specific drug targets, which function as saturable receptors. Particular drugs have characteristic affinities for such specific drug targets according to well known receptor-ligand (drug) binding interactions, on the basis of which drug affinity for a specific drug target may be determined (e.g., Rang, H. P. et al. (Eds.), Pharmacology, 2003 Churchill Livingstone, New York, Ch. 2). It is noteworthy that according to certain invention embodiments disclosed herein as may relate to a method for maintaining a desired concentration of one or more drugs (e.g., in a body compartment), the antibody dissociation constant $K_D$ is independent of affinity of the drug for a specific drug target. In this regard, the present invention may be clearly distinguished over the disclosure in U.S. 2002/0122810, the teachings of which are limited to prodrug complexes that rely upon the affinity of a natural receptor for a drug being higher relative to the affinity of a synthetic receptor for the drug. According to the presently disclosed embodiments, there is no such reliance upon drug affinity for a specific drug target in a subject. Instead, and as noted herein, according to the embodiments disclosed and claimed herein, the antibody dissociation constant $K_D$ is independent of affinity of the drug for a specific drug target.

Insofar as methodologies for determining an antibody dissociation constant, $K_D$, are described herein and known to the art (e.g., Weir, D. M., *Handbook of Experimental Immunology*, 1986, Blackwell Scientific, Boston; Harlow and Lane, *Antibodies: A Laboratory Manual*, Cold Spring Harbor Laboratory, 1988), according to certain preferred embodiments suitable antibodies may be selected on the basis of their having a $K_D$ value that is substantially similar to a drug concentration that is desired for use in a subject. Such values are substantially similar according to art-accepted criteria with regard to determination both of (i) a desired concentration range for a particular drug to be used for treatment of a particular indication, such as in a particular body compartment, and (ii) an antibody dissociation constant $K_D$ value as may be detectable using currently available methodologies and instrumentation. Accordingly it is preferred in certain embodiments for the substantially similar antibody dissociation constant $K_D$ to have a value that equals a value within the desired concentration range for the drug, while in other embodiments a substantially similar antibody $K_D$ value may be, in a statistically significant fashion, within tenfold of a drug concentration that is within the desired drug concentration range, more preferably within ninefold, eightfold, sevenfold, sixfold, fivefold, fourfold, threefold, twofold or less of a desired drug concentration, and in certain embodiments the $K_D$ value may be within or less than 1.75-fold, 1.5-fold, 1.25-fold or 0.5 to 1-fold of a drug concentration that is within the desired drug concentration range.

In certain related embodiments two or more antibodies may be selected having different antibody $K_D$ values, wherein each $K_D$ value may be substantially similar to a drug concentration that is within the desired drug concentration range but each such $K_D$ value represents a different concentration within the range. These and related further embodiments may permit fine-tuning of the use of antibody buffering to regulate drug concentrations in body compartments as described herein. According to non-limiting theory and as discussed above, such use of a plurality of antibodies, each having a distinct $K_D$ value that is substantially similar to a desired drug concentration that is within the desired concentration range for the drug, influences the rate of drug clearance within a body compartment by virtue of the antibody effect on equilibrium drug concentration. In a related embodiment, multimeric antibodies, for example, bispecific antibody molecules, may be engineered for use as buffering antibodies according to the instant disclosure, whereby a single antibody molecule may have two different antibody binding sites for antigen (drug), each of such sites having a distinct $K_D$ value that is substantially similar to a desired drug concentration that is within the desired concentration range for the drug. Persons knowledgeable in the art will be familiar with a variety of strategies for preparing bispecific and other multimeric antibodies (Peipp et al., 2002 *Biochem Soc. Transact* 30:507; Presta, 2002 *Curr. Pharm. Biotechnol.* 3:237) and diabodies (Kipriyanov, 2002 *Meths. Mol. Biol.* 178:317). Multimeric antibodies include bispecific and bifunctional antibodies comprising a first Fv specific for an antigen associated with a second Fv having a different antigen specificity (see, e.g., Drakeman et al., *Expert Opin. Investig. Drugs* 6:1169-78 (1997); Koelemij et al., *J. Immunother.* 22:514-24 (1999); Marvin et al., *Acta Pharmacol. Sin.* 26:649-58 (2005); Das et al., *Methods Mol. Med.* 109:329-46 (2005)).

Similarly, according to certain other embodiments two or more drugs may be indicated for treatment of a subject, such that it may be desirable to maintain a desired concentration range for each of the drugs using the in vivo antibody buffering provided by the present invention, in embodiments that are contemplated in view of the instant disclosure. For example, such a method may comprise administering at least one dose of a first drug and at least one first antibody, or an antigen-binding fragment thereof, that specifically binds to the first drug; and administering at least one dose of a second drug and at least one second antibody, or an antigen-binding fragment thereof, that specifically binds to the second drug.

Methods and compositions contemplated according to certain embodiments of the present invention may be useful for treating a subject, which in preferred embodiments may be a human subject and in other embodiments may be a non-human animal such as a mammal including non-human primates (e.g., chimpanzee, gorilla, macaque, monkey, etc.), livestock (e.g., horse, bovine, goat, sheep, pig, etc.) or other mammal (e.g., dog, cat, rabbit, hamster, guinea pig, gerbil, mouse, rat, etc.), or other non-mammalian animal species. Certain embodiments include a method for maintaining a desired concentration range of a drug in a subject that is a patient having a disease or disorder that is characterized by an abnormality or anomalous condition in a cell or tissue that is within a body compartment, such as a neoplastic condition.

Certain embodiments disclosed herein relate to a method for maintaining a desired concentration range of a drug in a body compartment in a subject which is a central nervous system compartment, including a subject diagnosed with a neoplastic condition within the CNS, but the invention is not intended to be so limited and contemplates treatment methods applicable to a wide range of other diseases, disorders and conditions as well. For example, antibody buffering methods and compositions as described herein may be usefully employed to maintain drug concentrations in a CNS compartment for treating metastases (e.g., metastatic brain tumors), a neurodegenerative disease (e.g., Alzheimer's disease, Parkinson's disease, Huntington's disease, amyotrophic lateral sclerosis, multiple sclerosis, and other diseases characterized by neurodegeneration), or a vascular disease (e.g., stroke, temporal arteritis) or to maintain drug concentrations in a body compartment for treating an autoimmune disease (e.g., multiple sclerosis and vasculitis in CNS compartments; rheumatoid arthritis and spondylitis in the joint capsule and/or bursa; Graves' disease in the thyroid; etc.), or for any other indication where maintaining a desired concentration range of a drug in a body compartment may be beneficial.

The presence of a neoplastic condition in a subject refers to the presence of dysplastic, cancerous and/or transformed cells in the subject, including, for example malignant, metastatic, tumor, non-contact inhibited and/or oncogenically transformed cells, or the like (e.g., glioma, astrocytoma, neurofibroma, neuroblastoma, lymphoma, melanoma, carcinomas such as adenocarcinoma, squamous cell carcinoma, small cell carcinoma, oat cell carcinoma, etc., sarcomas such as chondrosarcoma, osteosarcoma, etc.) which are known to the art and for which criteria for diagnosis and classification are established. In certain preferred embodiments contemplated by the present invention, for example, such cancer cells are neoplastic cells within a CNS compartment, such as transformed cells of brain parenchyma, meninges, cranial nerve, pituitary gland, pineal gland, oligodendroglia, ependyma and choroid plexus, and the like. Of particular relevance to these and related embodiments are brain metastases, including but not limited to metastases originating from small cell lung carcinoma, adenocarcinoma, lymphoma and other neoplasias.

Drugs/Pharmaceutical Composition and Administration

A drug for use according to the present invention may be any composition of matter that can be administered to a subject for therapeutic and/or diagnostic purposes. Preferably the drug is provided in soluble form. Without wishing to be bound by theory, a drug may specifically interact with its cognate specific drug target in a cell or tissue of the subject, to confer therapeutic benefit either directly as a result of the drug-target interaction (e.g., inhibition of an enzyme, blockade of a receptor), or indirectly (e.g., as a receptor agonist that initiates a signaling cascade to result in a desired event). Typically, drugs for use according to certain herein disclosed preferred embodiments include compounds known in the art as "small molecules" and having molecular weights less than $10^5$ daltons, preferably less than $10^4$ daltons, more preferably less than $8 \times 10^3$, $5 \times 10^3$, $3 \times 10^3$, $2 \times 10^3$ or $1.5 \times 10^3$ daltons, and still more preferably less than $10^3$ daltons.

For a particular disease or disorder, one or more drugs may be indicated as will be known to those familiar with the art, including suitable dosages from which a desired concentration range has been established (see, e.g., Physician's Desk Reference, 2004 Thompson Healthcare, NY; Beers and Berkow (Eds.), Merck Manual of Diagnosis and Therapy-$17^{th}$ Ed., 1999 John Wiley & Sons, NY). The invention need not, however, be so limited, and also contemplates new and/or experimental drugs for which a desired concentration range may be known or determined based upon available information or from readily generated data concerning pharmacological/pharmacokinetic, biological, chemical and other properties, as may be obtained from standard in vitro and in vivo methodologies using art-accepted systems. For instance, in vitro (e.g., cell culture-based) systems may establish minimum drug concentration ranges at which an effect on a cellular phenotype may be manifest, while in vivo models may be used according to conventional protocols to establish an upper limit of a drug concentration range, such as may be apparent from monitoring indicia of drug toxicity (e.g., necrosis, apoptosis, respiratory and/or metabolic impairment, or the like). Hence, once a drug or a combination of drugs is selected for treatment of a subject, the desired concentration range for each drug will be known based on the defined efficacious levels, and antibodies having appropriate antibody dissociation constant ($K_D$) values may be selected. Methods of generating antibodies are described herein and known in the art, as are methods for determining antibody dissociation constants, such that selecting antibodies having specific binding affinity for a desired cognate antigen (e.g., a ligand such as a drug) and further selecting from among such antibodies those having a $K_D$ that is substantially similar to a desired concentration that is within a desired drug concentration range, may be accomplished readily and without undue experimentation.

Accordingly, in certain embodiments the invention provides a method for identifying an antibody that is capable of maintaining a desired concentration range of a drug in a body compartment in a subject, comprising determining a desired concentration range of a drug to be maintained in a body compartment in the subject; and preparing an antibody that specifically binds to the drug and that has an antibody dissociation constant, $K_D$, having a value that is substantially similar to the desired concentration of the drug to be maintained in the body compartment, and thereby identifying an antibody that is capable of maintaining the desired concentration range of the drug.

Another unexpected advantage afforded by certain of the invention embodiments disclosed herein is the ability to maintain a desired concentration range of one or more drugs in a subject in vivo, for example, in a body compartment in the subject, for a desired period of time. As follows from the discussion above regarding antibody-antigen equilibrium dynamics, the surprising prolongation of drug half-life within a body compartment that results from the in vivo antibody buffering effect permits control of the duration over which a desired drug concentration may be maintained. Where the antibody dissociation constant $K_D$ controls the level of free (unbound) drug that may be attained as described herein, the absolute quantities of antibody and drug that are administered may be calculated in view of compartment volume and drug clearance rate (the pharmacokinetic rate of loss of free drug) for purposes of computing a time period over which a desired drug concentration range may be maintained.

The presently described methods for maintaining a desired concentration range of one or more drugs in a subject include doses of drugs and antibodies that may be formulated into pharmaceutical compositions for administration according to well known methodologies and techniques. In certain preferred embodiments, administration is to a body compartment. Pharmaceutical compositions generally comprise one or more drugs and/or antibodies, in combination with a pharmaceutically acceptable carrier, excipient or diluent. Such carriers will be nontoxic to recipients at the dosages and concentrations employed. For certain drugs and/or antibodies, about 0.01 µg/kg to about 100 mg/kg body weight will be administered, typically by a route determined according to the body compartment wherein maintenance of a desired concentration range of the drug(s) is to be effected, such as (for CNS) by intrathecal, intraventricular, epidural, subdural, subarachnoid, meningeal, sinusoidal or brain parenchymal administration, or (for other compartments) by direct injection into the pericardium, the pleural sac, the retro-orbital space, an ocular compartment such as one or more of the anterior chamber, posterior chamber or vitreous compartment of the eye, a joint capsule, a bursa, a lymphoid compartment such as the spleen, thymus or a lymph node, or a genitourinary compartment such as an ovary, a prostate gland, a scrotal sac or a testicle, or by inhalation of an aerosolized aqueous solution into an intranasal compartment, a bronchiolar or other lung compartment, or by other routes. According to certain preferred embodiments the body compartment comprises a central nervous system compartment and the step of administering comprises introduction of the drug intrathecally, intraventricularly, parenchymally, subdurally, subarachnoidally or epidurally.

A preferred dosage is about 1 µg/kg to about 1 mg/kg, with about 5 µg/kg to about 200 µg/kg particularly preferred. It will be evident to those skilled in the art that the number and frequency of administration will be dependent upon the response of the subject. As well, certain embodiments of the invention contemplate a method for maintaining a desired concentration range of one or more drugs in a body compartment in a subject comprising (a) administering to the body compartment simultaneously or sequentially and in either order (i) at least one dose of a drug and (ii) at least one antibody, or an antigen-binding fragment thereof, that specifically binds to the drug, wherein for said antibody an antibody dissociation constant, $K_D$, has a value that is substantially similar to the desired concentration of the drug, and wherein the antibody dissociation constant $K_D$ is independent of affinity of the drug for a specific drug target in the subject; and (b) subsequently administering at least one additional dose of the drug.

Further in this regard, given the surprising residence times of soluble antibodies in body compartment fluid volumes, at a time point where equilibrium calculations and/or empirical observations indicate that the combined effects of antibody-drug dissociation and drug clearance have reduced the drug level to below a desired concentration, repeated re-administration of free drug ("recharging") to a compartment in which antibody and drug have previously been administered is contemplated according to certain related embodiments comprising methods for maintaining a desired drug concentration. Without wishing to be bound by theory, under such circumstances a pool of anti-drug antibody, which has re-equilibrated in a body compartment to the point where drug concentration is low and excess antibody binding sites for drug are unoccupied by ligand (i.e., drug), may be available for such "recharging" with fresh drug, again resulting in prolonged maintenance of effective drug concentrations through the equilibrium principle of antibody buffering of a ligand in vivo. Such recharging also affords as an unexpected advantage a method whereby the body compartment, and thus the subject, are exposed at most to a transient and short-lived high level of the free drug, at the inception of the rapid equilibration process which leads to net sequestration of the drug in antibody-drug complexes.

Among the several invention embodiments described herein are included those in which (i) at least one dose of a drug and (ii) at least one antibody, or an antigen-binding fragment thereof, that specifically binds to the drug, may be administered simultaneously or sequentially and in either order. Other related embodiments may include those in which the drug and the antibody are admixed or premixed prior to administration, while still other related embodiments include those in which the antibody and the drug are separately administered, or are mixed at the time of administration.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and other ancillary agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id. "Pharmaceutically acceptable salt" refers to salts of drug compounds derived from the combination of such compounds and an organic or inorganic acid (acid addition salts) or an organic or inorganic base (base addition salts). The drugs contemplated for use herein may be used in either the free base or salt forms, with both forms being considered as being within the scope of the certain present invention embodiments.

The pharmaceutical compositions that contain one or more drugs and/or one or more antibodies may be in any form which allows for the composition to be administered to a patient. For example, the composition may be in the form of a solid, liquid or gas (aerosol). According to certain preferred embodiments the composition will be in liquid form and the route of administration will comprise administration to a body compartment simultaneously or sequentially and in either order at least one dose of a drug and at least one antibody, or an antigen-binding fragment thereof, that specifically binds to the drug. Other typical routes of administration may include, without limitation, oral, sublingual, topical, parenteral (e.g., sublingually or buccally), sublingual, rectal, vaginal, and intranasal. The term parenteral as used herein includes subcutaneous injections, intravenous, intramuscular, intramedullar, intrasternal, intracavemous, intrathecal, intrameatal, intraurethral injection or infusion techniques.

The pharmaceutical composition is formulated so as to allow the active ingredients contained therein to be bioavailable upon administration of the composition to a subject such as a human patient. Compositions that will be administered to a patient take the form of one or more doses or dosage units, where for example, a pre-measured fluid volume may comprise a single dosage unit, and a container of one or more compositions (e.g., drugs, anti-drug antibodies) in liquid or aerosol form may hold a plurality of dosage units. A dose of a drug includes all or a portion of a therapeutically effective amount of a particular drug that is to be administered in a manner and over a time sufficient to attain or maintain a desired concentration range of the drug, for instance, a desired concentration range of the drug in a body compartment, and where the absolute amount of the drug that comprises a dose will vary according to the drug, the subject, the body compartment, and other criteria with which the skilled practitioner will be familiar in view of the state of the medical and pharmaceutical and related arts. In certain embodiments at least two doses of the drug may be administered, and in certain other embodiments the antibody and the drug may be administered in approximately equimolar concentrations (i.e., equivalent concentrations according to current statistically significant detection limits, with less than 15 percent standard deviation, preferably less than 10 percent, more preferably less than 5 percent, still more preferably less than 3, 2, 1 or 0.1 percent). Other embodiments contemplate administering the antibody and the drug at an antibody-to-drug molar ratio of at least approximately 2:1, 2.5:1, 3:1, 4:1, 5:1 or greater than 5:1.

A liquid pharmaceutical composition as used herein, whether in the form of a solution, suspension or other like form, may include one or more of the following adjuvants: sterile diluents such as water for injection, saline solution, preferably physiological saline, Ringer's solution, saline solution (e.g., normal saline, or isotonic, hypotonic or hypertonic sodium chloride), fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile. It may also be desirable to include other components in the preparation, such as delivery vehicles including but not limited to aluminum salts, water-in-oil emulsions, biodegradable oil vehicles, oil-in-water emulsions, biodegradable microcapsules, and liposomes.

While any suitable carrier known to those of ordinary skill in the art may be employed in the pharmaceutical compositions of this invention, the type of carrier will vary depending on the mode of administration and whether, in addition to the biopharmacological buffering effect afforded by antibodies according to the present invention, a conventional sustained drug release is also desired. For parenteral administration, such as supplemental injection of drug, the carrier preferably comprises water, saline, alcohol, a fat, a wax or a buffer. Biodegradable microspheres (e.g., polylactic galactide) may also be employed as carriers for the pharmaceutical compositions of this invention. Suitable biodegradable microspheres are disclosed, for example, in U.S. Pat. Nos. 4,897, 268 and 5,075,109. In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Body Compartments

A body compartment may include any defined anatomic compartment that is substantially but not necessarily absolutely separated in its fluid communication from other regions of the body, for instance, as may be the product of tissue or organ architecture, such as a spatially defined compartment that may be separated from other body areas by a thin membrane (e.g., meningeal membrane, pericardial membrane, pleural membrane, periosteum, joint capsular membrane, mucosal membrane, basement membrane, peritoneal membrane, omentum, organ-encapsulating membrane, or the like). In certain preferred embodiments described herein, a body compartment may be a CNS compartment, which is physically and physiologically separated from the circulation by the blood brain barrier (Begley, 2004 *Pharmacol. Therapeut.* 104:29), and which may be accessed intrathecally, intraventricularly, parenchymally, subdurally, subarachnoidally or epidurally.

As a brief background, the blood brain barrier (BBB) profoundly influences the CNS penetration of most substances (Heideman et al., 1997 *Cancer* 80:497) and has been implicated in the failure of attempts to treat brain tumors with aggressive chemotherapy (Castro et al., 2003 *Pharmacol. Ther.* 98:71). Its purpose is to separate the brain from the blood to help regulate brain function and metabolism. The BBB is made up of tight endothelial cell junctions that limit penetration to all but small (less than 200 daltons), lipophilic, non-ionized compounds.

Cerebrospinal fluid (CSF) is the liquid that fills the ventricular system and the subarachnoid space. It is formed by the choroid plexuses through processes of osmosis and active transport. Proteins usually cannot pass through the choroid plexus, which prevents the passage of immunizing substances into the CSF. The direction of CSF flow is from the lateral ventricle, through the interventricular foramen, third ventricle, cerebral aqueduct, and into the fourth ventricle. Then it passes into the subarachnoid space where it is free to flow anywhere on the surface of the brain. The arachnoid proliferates to form macroscopic patches of branched arachnoidal villi which project into spaces within the dura or into the superior saggital venous sinus. It is through these arachnoid granulations that CSF is reabsorbed into the vascular system.

Despite the fact that currently available drugs used for intrathecal chemotherapy are rapidly cleared from the CSF (Jaeckle et al., 2002), the present application discloses the unexpected discovery that a buffering antibody, selected on the basis of having a dissociation constant that is substantially similar to a desired drug-concentration, can retard such clearance and thereby maintain the drug at or near its desired concentration. As also noted above, certain preferred embodiments will be especially useful in the treatment of CNS neoplasia, such as brain metastases, including but not limited to metastases originating from small cell lung carcinoma, adenocarcinoma, lymphoma and other malignancies.

Additional body compartments in which in vivo antibody buffering of a ligand (e.g., drug) may be practiced include the pericardium, pleural space, retro-orbital compartment, eye (further including anterior chamber, posterior chamber and vitreous compartment), joint capsule, bursa, lymphoid compartments (such as spleen, thymus and lymph node), the peritoneal cavity, the intranasal compartment, the lung, and genitourinary compartments such as ovary, prostate, and scrotum, and other comparably defined body compartments. Examples of body compartments are also described anatomically and pharmacokinetically in Ohning et al., 1995 *Neonatal. Netw.* 14:7; Ohning et al., 1995 *Neonatal. Netw.* 14:15; and in U.S. Pat. No. 6,414,033 and publications cited therein (e.g., Nordenstrom, B. E., Biologically Closed Electrical Systems: Clinical, Experimental and Theoretical Evidence of an Additional Circulatory System, Stockholm, Nordic Medical Publications, 1983; and Evans, E. E., Schentag J. J., Jusko W. J. (Eds.), Applied Pharmacokinetics: Principles of Therapeutic Drug Monitoring, 3rd ed, Vancouver, Wash., 1992). Therapeutic access to body compartments according to established routes, for purposes of administering at least one dose of a drug and at least one antibody, is within the repertoire of medical and veterinary arts according to therapeutic methods as described herein.

Antibodies

Also contemplated by the present invention are antibodies including anti-drug binding molecules that are peptides, polypeptides and other molecules that specifically bind to a drug. Such binding molecules can be used in a method for maintaining a desired concentration range of one or more drugs, as described herein. An antibody such as an anti-drug binding molecule is said to specifically bind to a particular drug if it reacts (e.g., binds) at a detectable level with the drug but does not react detectably with structurally distinct or unrelated molecules. Preferred binding molecules thus include antibodies, which may be, for example, polyclonal, monoclonal, single chain, chimeric, humanized, anti-idiotypic, or CDR-grafted immunoglobulins, or antigen-binding fragments thereof, such as proteolytically generated or recombinantly produced immunoglobulin $F(ab')_2$, Fab, Fab', Fv, and/or Fd fragments, single domain antibodies ("dAbs"; Holt et al., 2003 *Trends Biotech.* 21:484) and diabodies (Hudson et al., 1999 *J. Immunol. Meth.* 231:177). An antibody according to the present invention may belong to any immunoglobulin class, for example IgG, IgE, IgM, IgD, or IgA. It may be obtained from or derived from an animal, for example, fowl (e.g., chicken) or a mammal, which includes but is not limited to a mouse, rat, hamster, rabbit, or other rodent, a cow, horse, sheep, goat, camel, human, or other primate. The antibody may be an internalizing antibody, or the antibody may be modified so that it may be easily transported across a cell membrane.

Certain preferred antibodies are those antibodies that inhibit, hinder, or block a drug from interacting with its cognate specific drug target. Binding properties of an antibody to drug may generally be assessed using conventional immunodetection methods including, for example, an enzyme-linked immunosorbent assay (ELISA), immunoprecipitation, radioimmunoassays, immunoblotting and the like, which may be readily performed by those having ordinary skill in the art. A skilled artisan will also be familiar with such immunodetection methods which, when used to detect an antibody that binds to a conformational epitope of a drug ligand, may preferably avoid any reagent or condition which could potentially denature the drug and thus alter or destroy the ligand conformational epitope.

Methods well known in the art and described herein may be used to generate antibodies, including polyclonal antisera or monoclonal antibodies, that are specific for a particular drug as may be desired. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second, distinct mammalian species (see, e.g., Morrison et al., *Proc. Natl. Acad. Sci. USA,* 81:6851-55 (1984); Shin et al., *Methods Enzymol.* 178:459-76 (1989); Walls et al., *Nucleic Acids Res.* 21:2921-29 (1993); U.S. Pat. No. 5,482,856). Most commonly, a chimeric antibody has murine variable region sequences and human constant region sequences. Such a murine/human chimeric immunoglobulin may be "humanized" by grafting the complementarity determining regions (CDRs) derived from a murine antibody, which confer binding specificity for an antigen, into human-derived V region framework regions and human-derived constant regions (see, e.g., Jones et al., *Nature* 321:522-25 (1986); Riechmann et al., *Nature* 332:323-27 (1988); Padlan et al., *FASEB* 9:133-39 (1995); Chothia et al., *Nature,* 342:377-383 (1989); Bajorath et al., *Ther. Immunol.* 2:95-103 (1995); EP-0578515-A3). Fragments of these molecules may be generated by proteolytic digestion, or optionally, by proteolytic digestion followed by mild reduction of disulfide bonds and alkylation.

Alternatively, such fragments may also be generated by recombinant genetic engineering techniques (e.g., Harris, W. J., Adair, J. R., (Eds.) 1997 Antibody Therapeutics, CRC Press, Boca Raton, Fla.).

An antibody that is immunospecific or that specifically binds to a drug as provided herein reacts at a detectable level with the drug and not with molecules having distinct or unrelated structures, preferably with an affinity constant, $K_a$, of greater than or equal to about $10^4$ $M^{-1}$, more preferably of greater than or equal to about $10^5$ $M^{-1}$, more preferably of greater than or equal to about $10^6$ $M^{-1}$, and still more preferably of greater than or equal to about $10^7$ $M^{-1}$. Affinity of an antibody for its cognate antigen is also commonly expressed as a dissociation constant $K_D$, and an anti-drug antibody specifically binds to the drug if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of binding partners or antibodies can be readily determined using conventional techniques, for example, those described by Scatchard et al. (*Ann. N.Y. Acad. Sci. USA* 51:660 (1949)) or by surface plasmon resonance (BIAcore, Biosensor, Piscataway, N.J.). See, e.g., Wolff et al., *Cancer Res.* 53:2560-2565 (1993).

Antibodies may generally be prepared by any of a variety of techniques known to those skilled in the art. See, e.g., Harlow et al., *Antibodies: A Laboratory Manual*, Cold Spring Harbor Laboratory (1988). In one such technique, an animal is immunized with an immunogenic form of the drug, for instance, using the drug as a hapten on a suitable carrier according to established methodologies, as an antigen to generate polyclonal antisera. Suitable animals include, for example, rabbits, sheep, goats, pigs, cattle, and may also include smaller mammalian species, such as mice, rats, and hamsters, or other species.

An immunogen may comprise a purified or partially purified drug, or may be comprised of cells expressing the drug (e.g., for a drug which is a polypeptide or a polynucleotide or a metabolite) or to which the drug has been introduced in a manner to enhance its immunogenicity. Peptide or polypeptide drugs may be generated using standard recombinant genetic methodologies, or by proteolytic cleavage of naturally occurring proteins, or may be chemically synthesized. Peptide drugs may be isolated by techniques known in the art such as polyacrylamide gel electrophoresis or any of a variety of other separation methods such as liquid chromatography or other suitable methodologies.

For raising antibodies to drugs that are polypeptides or peptides, peptides useful as immunogens typically may have an amino acid sequence of at least 4 or 5 consecutive amino acids from the drug sequence, and preferably have at least 6, 7, 8, 9, 10, 11, 12, 14, 15, 16, 18, 19 or 20 consecutive amino acids of the drug polypeptide sequence. Certain other preferred peptide immunogens may comprise 21-25, 26-30, 31-35, 36-40, 41-50 or more consecutive amino acids of a drug polypeptide sequence. Polypeptides or peptides useful for immunization may also be selected by analyzing the primary, secondary, and tertiary structure of drug polypeptide according to methods known to those skilled in the art, in order to determine amino acid sequences more likely to generate an antigenic response in a host animal. See, e.g., Novotny, 1991 *Mol. Immunol.* 28:201-207; Berzofsky, 1985 *Science* 229:932-40; Chang et al. *J. Biochem.* 117:863-68 (1995); Kolaskar et al. *Viology* 261:31-42 (1999)). Preferably, the polypeptide or peptide comprises a sufficient number of amino acids to fold in a manner that approximates the conformation of the drug polypeptide in its pharmacologically active form.

Immunogens may be prepared and animals immunized according to methods well known in the art. See, e.g., Harlow et al., *Antibodies: A Laboratory Manual*, Cold Spring Harbor Laboratory (1988). The immune response may be monitored by periodically bleeding the animal, separating the sera out of the collected blood, and analyzing the sera in an immunoassay, such as an ELISA or Ouchterlony diffusion assay, or the like, to determine the specific antibody titer. Once an antibody titer is established, the animals may be bled periodically to accumulate the polyclonal antisera. Polyclonal antibodies that bind specifically to the drug may then be purified from such antisera, for example, by affinity chromatography using *S. aureus* protein A or protein G, which specifically binds to a constant region (heavy or light chain) of the antibody(ies) to be purified, or using the drug, immobilized on a suitable solid support.

Monoclonal antibodies that specifically bind to drug and hybridomas, which are immortal eukaryotic cell lines, that produce monoclonal antibodies having the desired binding specificity, may also be prepared, for example, using the technique of Kohler and Milstein (*Nature*, 256:495-497; 1976, *Eur. J. Immunol.* 6:511-519 (1975)) and improvements thereto with which a skilled artisan will be familiar. An animal—for example, a rat, hamster, or a mouse—is immunized with a drug or drug immunogen; lymphoid cells that include antibody-forming cells, typically spleen cells, are obtained from the immunized animal; and such cells may be immortalized by fusion with a selection agent-sensitized myeloma (e.g., plasmacytoma) cell fusion partner.

Monoclonal antibodies may be isolated from the supernatants of hybridoma cultures or isolated from a mouse that has been treated (e.g., pristane-primed) to promote formation of ascites fluid containing the monoclonal antibody. Antibodies may be purified by affinity chromatography using an appropriate ligand selected based on particular properties of the monoclonal antibody (e.g., heavy or light chain isotype, binding specificity, etc.). Examples of a suitable ligand, immobilized on a solid support, include Protein A, Protein G, an anti-constant region (light chain or heavy chain) antibody, an anti-idiotype antibody and the drug antigen for which specific antibodies are desired.

Human monoclonal antibodies may be generated by any number of techniques with which those having ordinary skill in the art will be familiar. Antibodies may also be identified and isolated from human immunoglobulin phage libraries, from rabbit immunoglobulin phage libraries, and/or from chicken immunoglobulin phage libraries (see, e.g., Winter et al., 1994 *Annu. Rev. Immunol.* 12:433-55; Burton et al., 1994 *Adv. Immunol.* 57:191-280; U.S. Pat. No. 5,223,409; Huse et al., 1989 *Science* 246:1275-81; Schlebusch et al., 1997 *Hybridoma* 16:47-52 and references cited therein; Rader et al., *J. Biol. Chem.* 275:13668-76 (2000); Popkov et al., *J. Mol. Biol.* 325:325-35 (2003); Andris-Widhopf et al., *J. Immunol Methods* 242:159-31 (2000)), or by other methodologies such as ribosome display (e.g., Hanes et al., 1998 *Proc. Nat. Acad. Sci. USA* 95:14130) or yeast display (e.g., Colby et al., 2004 *Meths. Enzymol.* 388:348) or the like. Antibodies isolated from non-human species or non-human immunoglobulin libraries may be genetically engineered according to methods described herein and known in the art to "humanize" the antibody or fragment thereof.

In certain embodiments, a B cell from an immunized animal that is producing an anti-drug, drug, or an anti-mutant drug, including an anti-double mutant drug, antibody is selected and the light chain and heavy chain variable regions are cloned from the B cell according to molecular biology techniques known in the art (WO 92/02551; U.S. Pat. No.

5,627,052; Babcook et al., *Proc. Natl. Acad. Sci. USA* 93:7843-48 (1996)) and described herein. Preferably B cells from an immunized animal are isolated from the spleen, lymph node, or peripheral blood sample by selecting a cell that is producing an antibody that specifically binds to drug or to a double mutant drug. B cells may also be isolated from humans, for example, from a peripheral blood sample.

An antibody fragment may also be any synthetic or genetically engineered protein that acts like an antibody in that it binds to a specific antigen to form a complex. For example, antibody fragments include isolated fragments consisting of the light chain variable region; "Fv" fragments consisting of the variable regions of the heavy and light chains; recombinant single chain polypeptide molecules in which light and heavy variable regions are connected by a peptide linker (scFv proteins); and minimal recognition units consisting of the amino acid residues that mimic the hypervariable region. Such an antibody fragment preferably comprises at least one variable region domain. (see, e.g., Bird et al., *Science* 242: 423-26 (1988); Huston et al., *Proc. Natl. Acad. Sci. USA* 85:5879-5883 (1988); EP-B1-0318554; U.S. Pat. No. 5,132, 405; U.S. Pat. No. 5,091,513; and U.S. Pat. No. 5,476,786).

In certain embodiments, an antibody that specifically binds to a drug may be an antibody that is expressed as an intracellular protein. Such intracellular antibodies are also referred to as intrabodies and may comprise an Fab fragment, or preferably comprise a scFv fragment (see, e.g., Lecerf et al., *Proc. Natl. Acad. Sci. USA* 98:4764-49 (2001)). The framework regions flanking the CDR regions can be modified to improve expression levels and solubility of an intrabody in an intracellular reducing environment (see, e.g., Worn et al., *J. Biol. Chem.* 275:2795-803 (2000)). An intrabody may be directed to a particular cellular location or organelle, for example by constructing a vector that comprises a polynucleotide sequence encoding the variable regions of an intrabody that may be operatively fused to a polynucleotide sequence that encodes a particular target antigen within the cell (see, e.g., Graus-Porta et al., *Mol. Cell Biol.* 15:1182-91 (1995); Lener et al., *Eur. J. Biochem.* 267:1196-205 (2000)). An intrabody may be introduced into a cell by a variety of techniques available to the skilled artisan including via a gene therapy vector, or a lipid mixture (e.g., Provectin™ manufactured by Imgenex Corporation, San Diego, Calif.), or according to photochemical internalization methods.

The polynucleotides encoding an antibody or fragment thereof that specifically bind a drug, as described herein, may be propagated and expressed according to any of a variety of well-known procedures for nucleic acid excision, ligation, transformation, and transfection using any number of known expression vectors. Thus, in certain embodiments expression of an antibody fragment may be preferred in a prokaryotic host, such as *Escherichia coli* (see, e.g., Pluckthun et al., 1989 *Methods Enzymol.* 178:497-515). In certain other embodiments, expression of the antibody or a fragment thereof may be in a eukaryotic host cell, including yeast (e.g., *Saccharomyces cerevisiae, Schizosaccharomyces pombe*, and *Pichia pastoris*), fungi (e.g., *Neurospora* cells such as those of *N. crassa*) animal cells (including mammalian cells) or plant cells. Examples of suitable animal cells include, but are not limited to, myeloma, COS, CHO, or hybridoma cells. Examples of plant cells include tobacco, corn, soybean, and rice cells.

Antibodies that specifically bind to the drug may be screened in assays for determining antibody affinity as described above, such as assays for determining $K_d$ of an antibody, to identify antibodies that have a $K_d$ value that is substantially similar to the desired concentration of a drug that is to be maintained in a body compartment. Antibodies so selected and that specifically bind to a drug may be used in methods described herein for maintaining a desired concentration range of one or more drugs in a subject, including in a body compartment in a subject.

The following Examples are offered by way of illustration and not limitation.

EXAMPLES

Example 1

Antibody Buffering in the Cerebrospinal Fluid

Methods

Antibody Production. The anti-Ox hybridoma NQ11/7.12 has been described previously (Griffiths et al., *Nature* 312: 271-75 (1984; Berek et al., *Eur. J. Immunol.* 17:1121-29 (1987)). A control (non-Ox binding) murine anti-lysozyme antibody, D1.3, (Amit et al., *Science* 233:747-53 (1986)) was also used. The hybridomas were grown in oscillating bubble roller bottles (Pannell et al., *J. Immunol. Methods* 146:43-48 (1992)), and the respective monoclonal antibodies were purified from spent culture supernatant by affinity chromatography on Protein A-Sepharose. SDS-PAGE was performed on the antibodies to verify purity. The protein concentration was determined by UV spectroscopy, using extinction coefficients calculated from sequence (Perkins, *Eur. J. Biochem.* 157:169-80 (1986)). Antibody solutions were filter-sterilized and stored at 4° C. under nitrogen.

Preparation of the tritiated 2-phenyl-oxazol-5-one-γ-amino butyrate conjugate (Ox). Crude Ox was prepared essentially as described by Berek et al., supra. $^3$H-γ-aminobutyric acid (GABA) (1 mCi/ml) was obtained from PerkinElmer Life Sciences, Inc., (Wellesley, Mass.) and solutions of unlabeled GABA (0.5 mM in 1 M $NaHCO_3$) and 4-ethoxy-methylene-2-phenyl-oxazolin-5-one (36.26 mg/ml in acetone) were prepared. Five μl of unlabeled GABA solution was mixed with 50 μl $^3$H-GABA on ice. Ten μl 4-ethoxy-methylene-2-phenyl-oxazolin-5-one solution was added and the reaction mixture was kept on ice for one hour with occasional hand mixing. Then, another 11 μl 4-ethoxy-methylene-2-phenyl-oxazolin-5-one solution was added, and the reaction mixture was left on ice for 20 minutes. Five μl of unlabeled GABA solution was added, and the reaction was brought to room temperature for 20 hours with fast mixing. One μl of concentrated acetic acid was then added; the resulting precipitate was dried in a ThermoSavant SPD1010 SpeedVac System with no heating. The dried precipitate was dissolved in PBS (25 mM $NaH_2PO_4$/125 mM NaCl, pH 7.0).

The resulting Ox product was purified using HPLC. 0.1 M ammonium formate, pH 4.8 (mobile phase A) and acetonitrile (mobile phase B) were vacuum-filtered through a 0.2 micron filter prior to use. Ox was applied to a Zorbax SB-C18 HPLC column with an analytical guard column from Agilent Technologies and eluted with 0.1 M ammonium formate, pH 4.8 (mobile phase A) and acetonitrile (mobile phase B). A gradient of 9.5% to 70% mobile phase B over 26 minutes was run at a flow rate of 0.5 ml/min and the eluate was monitored using a wavelength of 348 nm. The Ox peak eluted at 20.5 minutes. Its identity was confirmed by scintillation counting of the fractions collected in that peak. Pooled fractions from the Ox peak were dried in a SpeedVac system with no heat. After drying, the residue was resuspended in 1 ml PBS. The radiochemical purity of the Ox was confirmed by HPLC. The concentration was determined both by quantitative HPLC and by UV spectroscopy. Specific activity was determined by diluting 1 µl of Ox into 5 ml of Scintiverse II (Fisher Scientific) and counting in a Beckman LS6500 Scintillation Counter. The specific activity of Ox was $4.2 \times 10^6$ cpm/nmol.

Determination of anti-Ox antibody affinity at 37° C. Antibody affinities were determined by fluorescence spectroscopy (Foote and Milstein, *Nature* 352:530-32 (1991)) using a PerkinElmer LS 50 B luminescence spectrometer. Temperature control of the cuvette block was maintained by a circulating water bath heated to 37° C. A cuvette containing 20 nM NQ11/7.12 in PBS was placed in the spectrometer and allowed to equilibrate to 37° C. Thirty µg/ml ubiquitin was added as a carrier. An excitation wavelength of 280 nm with a bandwidth of 5 nm and an emission wavelength of 340 nm with a 10 nm bandwidth were used with an 8 second integration time. Ox-GABA solution was added in 40 nM increments and fluorescence readings were taken after allowing time for equilibration. The resulting concentration/fluorescence readings were analyzed by least squares (Foote and Winter, *J. Mol. Biol.* 224:487-99 (1992)) to determine the $K_d$ of each antibody.

Animals. Male Sprague-Dawley rats (300 g) were obtained from Zivic Laboratories, Inc. (Zelienople, Pa.). Each rat underwent surgery to place a cannula in the right lateral ventricle for injections and a second cannula in the cisterna magna for cerebral spinal fluid (CSF) sampling. Briefly, the rat was anesthetized with 2.5% isoflurane and fixed in a stereotaxic device. Normal body temperature was maintained through a heating pad. A linear midline incision exposed the frontal, parietal, and occipital bones. The lateral ventricle was located using the coordinates (1.8 mm posterior, 3.8 mm lateral, and 4 mm ventral from bregma) obtained from a stereotaxic atlas of the rat (Paxinos et al. *The Rat Brain in Stereotaxic Coordinates* (Academic Press 1998)). A hole was drilled through the skull, a cannula was inserted, and it was fixed to the skull using VetBond (3M, Minneapolis, Minn.) and dental cement. The hole was drilled for the cisternal cannula just posterior to the occipital crest and slightly left of midline to avoid puncture of the superior saggital sinus. The cannula was inserted to a depth of 2 mm below the bottom of the skull and fixed with VetBond and dental cement. Screw-capped cannula dummy wires were inserted into the cannula guides to maintain a closed system. Rats were allowed to recover for at least 24 hours before ventricular injection.

For experiments for which injections and withdrawals of CSF were done via the same site in the cisterna magna (CM), male Sprague-Dawley rats (250 g) were obtained from Charles River Laboratories (Wilmington, Mass.). These rats had a single cannula implanted into the cisterna magna using a procedure similar to that described above. Rats were allowed to rest no more than three days after arrival prior to experimentation to reduce the risk of cannula blockage.

Antibody Buffering Protocol. Samples were prepared for injection: 104 pmol anti-Ox antibody and 52 pmol Ox; 104 pmol of D1.3 control antibody and 52 pmol Ox; and 52 pmol Ox alone. Each sample was diluted to 10 µl with sterile PBS. The samples were warmed to 37° C., and then infused over 1 minute through the intraventricular or cisternal cannula in Sprague-Dawley rats. The end of the infusion was designated as time zero (0). At various timepoints, 10 µl of CSF was withdrawn. For one set of rats, the 10 µl CSF was counted directly by placing it into 5 ml of Scintiverse II and counting in a Beckman LS6500 Scintillation Counter. For another set of rats, the 10 µl CSF was diluted into 100 µl ice cold PBS and used in bound vs. free Ox experiments described below.

Separation of bound and free Ox using 187.1-Sepharose affinity resin. The rat anti-mouse kappa antibody 187.1 (obtained from American Type Culture Collection (ATCC), Manassas, Va.) (Yelton et al., *Hybridoma* 1:5-11 (1981)) was isolated from spent culture medium and purified by passage over a Protein A-Sepharose affinity column. Ten grams of CNBr-activated Sepharose 4 Fast Flow (Amersham Biosciences) were washed and coupled with 187.1 according to manufacturer's protocol. Two mg 187.1 per 10 g of swelled resin were used.

During the antibody buffering experiments, the CSF plus ice cold PBS sample were loaded onto the 187.1 column immediately after the dilution. Application to the column of 3 ml of PBS in 0.5 ml increments was followed by application of 3 ml of 0.2 M glycine (pH 2.5) in 0.5 ml increments. All the PBS fractions and all the glycine fractions were collected separately for each timepoint and dried down in the Speed-Vac. The residue was resuspended in 150 µl PBS and then transferred to a scintillation vial with 5 ml Scintiverse II for counting.

Long term antibody buffering protocol. Samples of NQ11/7.12 and Ox were prepared and infused into the cisternal cannula of Sprague-Dawley rats from Charles River Laboratories as described above for the antibody buffering protocol. Ten µl of CSF was taken from the cisterna magna at time 1, 10, 20, 30, 60, 90 and 120 minutes. The 10 µl CSF samples were either counted directly or diluted into 100 µl ice cold PBS and loaded onto a 187.1 column to separate bound and free Ox. At 24 hours and at 48 hours following the first administration, 52 pmol Ox in 10 µl total volume (diluted with sterile PBS) was infused over 1 minute through the cisterna magna cannula. Timepoints were again taken and analyzed as above.

Pharmacokinetic Analysis of Anti-Ox Antibody from the Cisterna Magna. A kinetically-characterized monoclonal antibody (NQ11/7.12) that specifically bound to Ox (Foote and Milstein, supra) was used to examine the effect of adding an anti-Ox antibody to the CSF. The affinity of this antibody was determined at 37° C. using fluorescence spectroscopy as described above and found to be 1.3 nM (NQ11/7.12). An isotype-matched (IgG$_1$) anti-hen-egg lysozyme antibody, D1.3 (Amit et al., *Science* 233:747-53 (1986)), was used as a control. Each rat in these studies was used only once to limit the possibility of a rat anti-mouse antibody response.

NQ11/7.12 was iodinated with $^{125}$I using the Chloramine T method (see Hunter et al., *Nature* 194:495-96 (1962); McConahey et al., *Methods Enzymol.* 70(A):210-13 (1980)). Iodine incorporation into the antibody was 97%, and the specific activity of the antibody solution was $1.25 \times 10^6$ cpm/µg. $^{125}$I-NQ11/7.12 (21.3 pmol) was mixed with unlabeled NQ11/7.12 to a final amount of 1.04 nmol. The sample was infused by hand over 1 minute through the cisternal cannula of the Charles River rats, and the cannula was flushed with 2 µl of normal saline. The end of the infusion was designated as time zero (0). Ten µl of CSF was withdrawn from the cisternal cannula at various timepoints. The entire CSF sample was counted using a Packard Cobra Auto-Gamma to determine the concentration of NQ11/7.12 in the CSF. The data are presented in FIG. 1. The anti-Ox monoclonal antibody (NQ11/7.12) in the CSF had a significantly longer half-life than the pharmacokinetic lifetime of most drugs. The concentration of NQ11/7.12 declined slowly with an elimination half-life from the CSF of 1 hour. Although this rate was similar to the rate of CSF bulk flow, it was significantly longer than that of Ox.

The Effect of NQ11/7.12 on Ox Lifetime in Rat CSF To determine the pharmacokinetic behavior of Ox in the CSF, tritiated Ox was infused into a rat through its intraventricular cannula, and elimination of Ox was followed through CSF sampling from the cisterna magna (CM) cannula. Sampling was done from the cisterna magna because it is the largest CSF compartment. Its location between the cerebellum and the upper brain stem and its large size make it relatively easy to access CSF for sampling and scintillation counting (van den Berg et al., *J. Neurosci. Methods* 116:99-107 (2002)).

Figure 2:
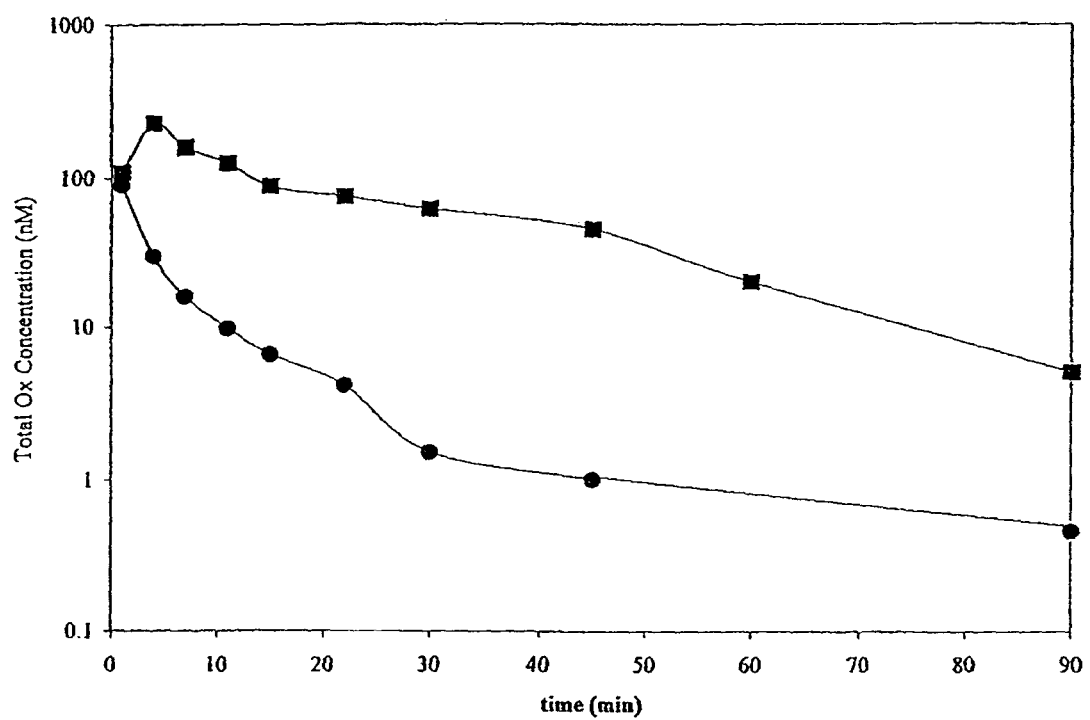
FIG. 2 shows buffering by the anti-Ox antibody NQ11/7.12 of interventricularly administered Ox. Ox was infused into animals with NQ11/7.12 (squares) or without antibody (circles). CSF samples were withdrawn from the cisterna magna.

For one set of five rats, Ox was administered either alone or with twice the molar amount of NQ11/7.12 through the intraventricular cannula. In the presence of specific antibody NQ11/7.12, cisternal CSF sampling showed the rise and fall of Ox concentration as it entered the CM, peaked in concentration at around 5 minutes, and then was eliminated. In the absence of NQ11/7.12, the concentration of Ox declined rapidly from the cisterna magna with an elimination half-life of 1.2 minutes (FIG. 2). This short lifetime indicated elimination by a mechanism much faster than the bulk flow of CSF. Ox that was not administered with an antibody buffer never attained a peak concentration in the CM. Rather, its elimination was so rapid that much had been eliminated before the Ox ever reached the CM.

Figure 3:
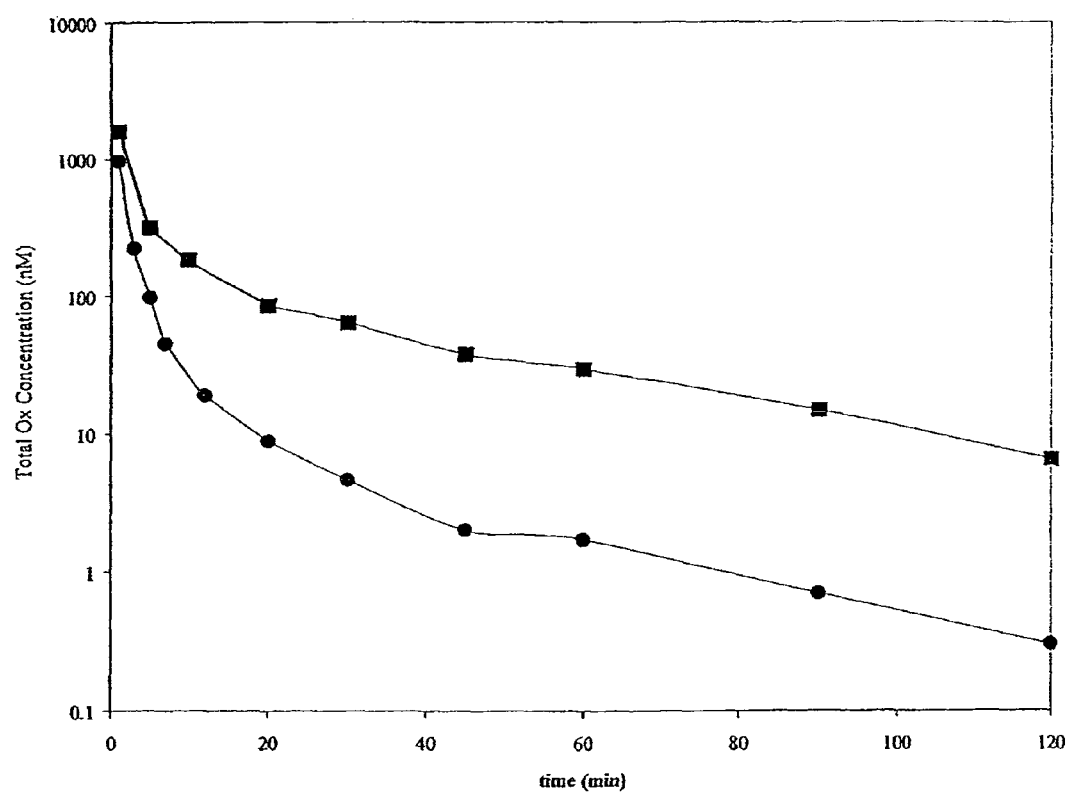
FIG. 3 illustrates buffering of Ox in the CSF by the anti-Ox antibody NQ11/7.12 when Ox was infused with antibody (squares) or without antibody (circles) into the cisterna magna of rats. CSF samples were withdrawn from the cistern and the radioactivity of $^3$H-GABA-Ox counted to determine total Ox concentration.

In a second experiment, Ox was infused through the rat's cisternal cannula. Ox was again co-administered with twice the molar amount of NQ11/7.12 or the control antibody. As shown in FIG. 3 administration of Ox with NQ11/7.12 showed a significant prolongation of Ox residence time with an Ox elimination half-life of 10 minutes. The Ox administered with D1.3 was eliminated from the CSF with a half-life of 1.0 minutes. This ten-fold increase in half-life indicates that NQ11/7.12 binding is opposing Ox elimination from the CSF.

Figure 4:
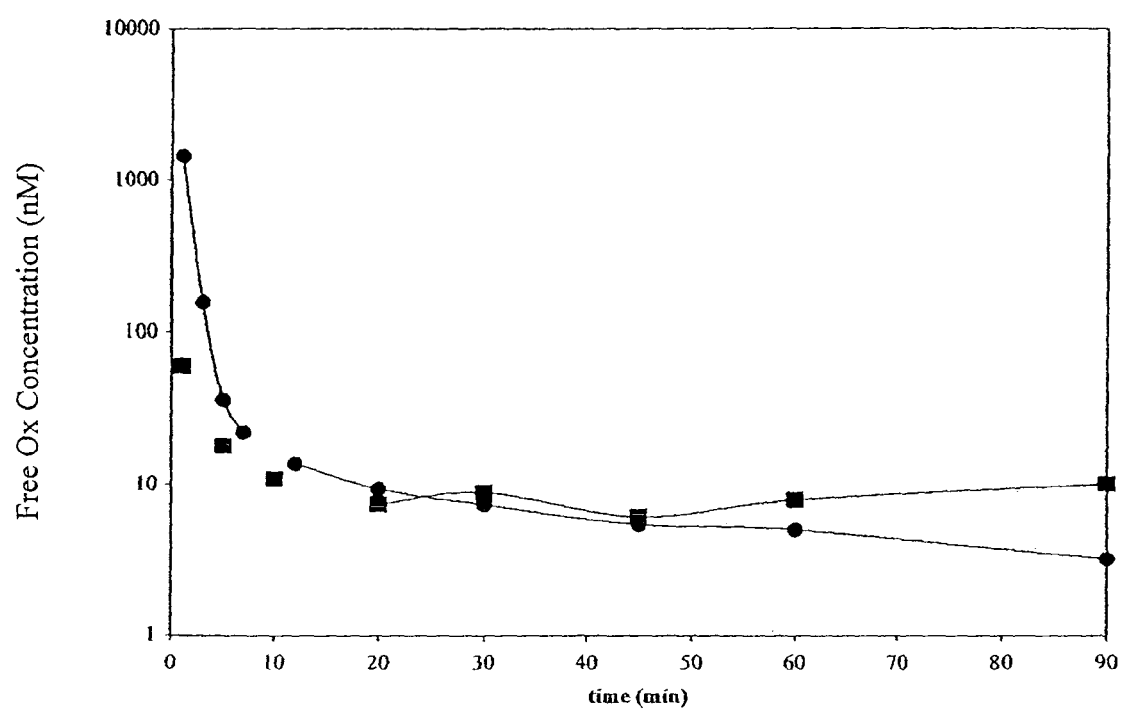
FIG. 4 shows the concentration of free Ox in the CSF of rats after administration of Ox with the anti-Ox antibody NQ11/7.12 (squares) and without antibody (circles).

The effect of NQ11/7.12 on free Ox concentration. The principle of chemical equilibrium predicts that the Ox in the CSF should partition between free and antibody-bound forms, and that the free pool should be constantly replenished, staying at a concentration near the antibody's $K_d$. The Ox in the CSF samples from another set of rats was separated into bound and free forms by passage over an affinity column. Samples from D1.3 co-administered with Ox were processed in parallel, though no significant antibody-bound label was expected or found. Antibody-Ox complexes bound to the immobilized rat anti-mouse kappa antibody while free Ox eluted from the column with the PBS wash (free Ox fraction). This analysis confirmed that a free pool of Ox existed in the rat CSF whether the Ox is administered with D1.3 or with NQ11/7.12 as shown in FIG. 4. Initially, when Ox was administered alone or with D1.3 the amount of free Ox was high (1.4 mM), but it quickly decreased 500 fold in an hour with an elimination half-life of 0.61 minutes. However, when Ox was administered with NQ11/7.12, the initial free concentration of Ox was low (60 nM). This low concentration remained fairly stable over time (decreasing less than 10-fold to approximately 6 nM) with an Ox elimination half-life of 1.55 minutes. Therefore, NQ11/7.12 appeared to be buffering free Ox according to the herein described equilibrium principle of antibody buffering of a ligand.

Figure 5A:
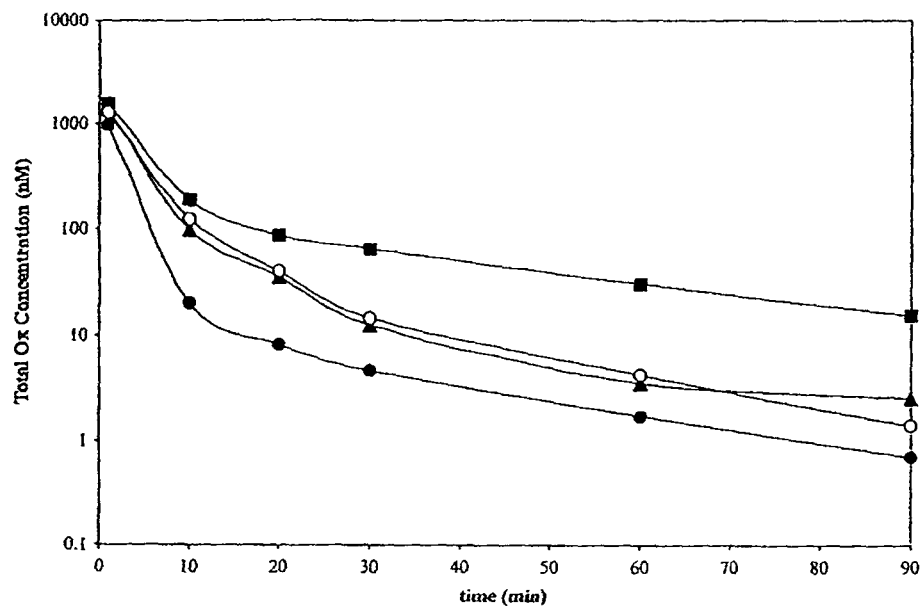
FIG. 5A presents the total Ox concentration in the CSF.
Figure 5B:
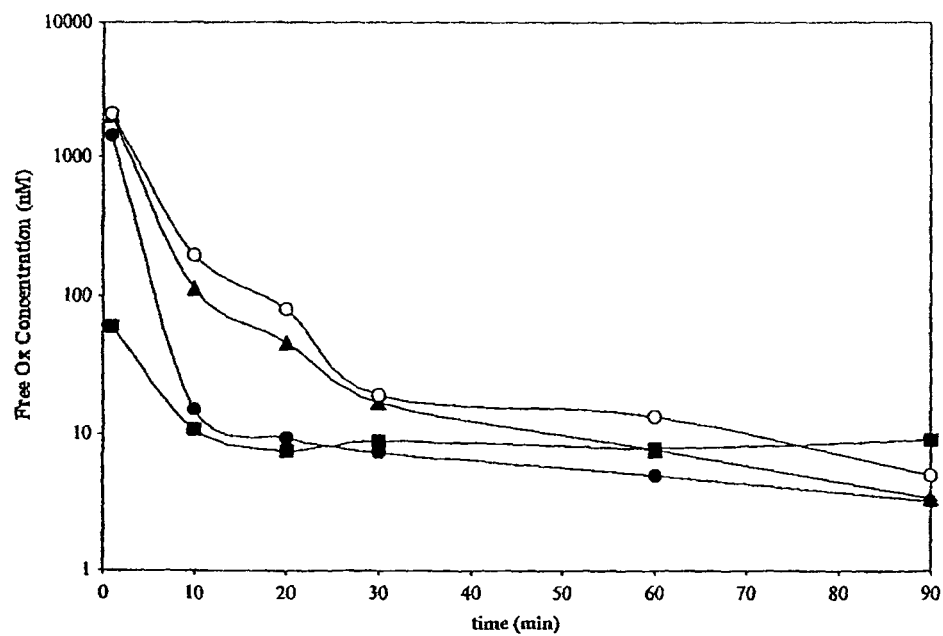
FIG. 5B presents the concentration of free Ox in the CSF.

Long Term Antibody Buffering. For these experiments, NQ11/7.12 was administered only once. Ox was initially co-administered with NQ11/7.12, and additional aliquots of Ox alone were administered at 24 hours and at 48 hours through the cisternal cannula. Cisternal CSF samples were collected to follow total Ox elimination from the CSF. As shown in FIG. 5A, the pharmacokinetic lifetime of Ox when administered at 24 hours and at 48 hours showed a kinetic profile between the profile observed when Ox was initially administered with NQ11/7.12 and the profile of Ox when administered with D1.3. This observation was likely, according to non-limiting theory, to be attributed to the slow clearance of circulating antibody overtime. Free vs. bound Ox separation was also performed on another set of CSF samples; the data are presented in FIG. 5B. Initially, the free Ox concentration at 24 hours and 48 hours was higher than when Ox was administered in conjunction with the antibody buffer. However, this free concentration decreased and Ox showed a slower elimination profile than Ox administered with D1.3. This observation was apparently the result of antibody initially binding Ox, which was at an initially high free Ox concentration, and antibody then subsequently releasing Ox overtime. Therefore, the anti-Ox antibody was capable of buffering the concentration of free Ox in the CSF days after the initial antibody infusion, according to the herein described equilibrium principle of antibody buffering of a ligand.

Example 2

Antibody Buffering of a Small Molecule

Methods

Antibodies. A panel of three anti-Ox hybridomas (NQ11/7.12, NQ16/113.8, NQ22/16.4) has been described previously (Griffiths et al., supra; Berek et al., supra). A control (non-Ox binding) murine anti-lysozyme antibody, D1.3, (Amit et al., supra) was also used. These hybridomas were grown in oscillating bubble roller bottles (Pannell and Milstein, supra) and the respective monoclonal antibodies were purified from spent culture supernatant by affinity chromatography on Protein A-Sepharose (see also Example 1). SDS-PAGE was performed on the antibodies to verify purity. Protein concentration was determined by UV spectroscopy using extinction coefficients calculated from sequence (Perkins, supra). Antibody solutions were filter-sterilized and stored at 4° C. under $N_2$.

Preparation of the tritiated 2-phenyl-oxazol-5-one-γ-amino butyrate conjugate (Ox). Crude Ox was prepared as described in Example 1 (Berek et al., supra). $^3$H-γ-aminobutyric acid (GABA) (1 mCi/ml) was obtained from PerkinElmer Life Sciences, Inc., and solutions of unlabeled GABA (0.5 mM in 1 M $NaHCO_3$) and 4-ethoxy-methylene-2-phenyl-oxazolin-5-one (0.17 M in acetone) were prepared. Five μl of unlabeled GABA solution were mixed with 50 μl $^3$H-GABA on ice. Ten μl 4-ethoxy-methylene-2-phenyl-oxazolin-5-one solution was added, and the reaction mixture was kept on ice for one hour with occasional hand mixing. Then, another 11 μl $^{14}$-ethoxy-methylene-2-phenyl-oxazolin-5-one solution were added and the reaction mixture was left on ice for 20 minutes. Five μl of unlabeled GABA solution was added and the reaction was brought to room temperature for 20 hours with fast mixing. One μl of concentrated acetic acid was then added; the resulting precipitate was dried in a ThermoSavant SPD1010 SpeedVac System with no heating. The dried precipitate was dissolved in PBS (25 mM $NaH_2PO_4$/125 mM NaCl, pH 7.0).

The resulting Ox product was purified using HPLC. 0.1 M ammonium formate, pH 4.8 (mobile phase A) and acetonitrile (mobile phase B) were vacuum-filtered through a 0.2 micron filter prior to use. Ox was applied to a Zorbax SB-C 18 HPLC column with an analytical guard column from Agilent Technologies and eluted with 0.1 M ammonium formate, pH 4.8 (mobile phase A) and acetonitrile (mobile phase B). A gradient of 9.5% to 70% mobile phase B over 26 minutes was run at a flow rate of 0.5 ml/min and using a wavelength of 348 nm. The Ox peak eluted at 20.5 minutes. Its identity was confirmed by measuring the radioactivity of the fractions collected in that peak. Pooled fractions from the Ox peak were dried in a ThermoSavant SPD1010 SpeedVac System with no heat. After drying, the residue was resuspended in 1 ml PBS.

The radiochemical purity of the Ox was confirmed by HPLC. The concentration was determined both by quantitative HPLC and by UV spectroscopy. Specific activity was determined by diluting 1 µl of Ox into 5 ml of Scintiverse II (Fisher Scientific) and counting in a Beckman LS6500 Scintillation Counter. The specific activity of Ox was $4.4 \times 10^6$ cpm/nmol.

Determination of anti-Ox antibody affinity at 37° C. Antibody affinities were determined by fluorescence spectroscopy as described in Example 1 (Foote and Milstein, supra) using a PerkinElmer LS 50 B luminescence. Temperature control of the cuvette block was maintained by a circulating water bath heated to 37° C. A cuvette containing either 20 nM (NQ11/7.12) or 200 nM (NQ16/113.8 or NQ22/16.4) in PBS was placed in the spectrometer and allowed to equilibrate to 37° C. In the case of NQ11/7.12, 30 µg/ml ubiquitin was added as a carrier. An excitation wavelength of 280 nm with a bandwidth of 5 nm and an emission wavelength of 340 nm with a 10 nm bandwidth were used with an 8 second integration time. Ox-GABA solution was added in 40 nM increments and fluorescence readings were taken after allowing time for equilibration. The resulting concentration/fluorescence readings were analyzed by least squares (Foote and Winter, supra) to determine the $K_d$ of each antibody.

Determination of anti-Ox antibody half-life in rat plasma. NQ11/7.12 was iodinated with $^{125}$I using the Chloramine T method (Hunter and Greenwood, supra; McConahey and Dixon, supra). Iodine incorporation into the antibody was 97%, and the specific activity of the antibody solution was $1.25 \times 10^6$ cpm/µg. Rats (300 g Sprague-Dawley males, Zivic Laboratories, Zelionople, Pa.) were implanted with a jugular vein cannula. The animals were allowed to rest at least 72 hours after delivery before experiments were started and allowed to move freely throughout the experiment. $^{125}$I-NQ11/7.12 (0.39 nmol) was mixed with unlabeled NQ11/7.12 to a final amount of 4.54 nmol. This amount was further diluted to a final volume of 1 ml in sterile PBS. The sample was infused by hand over 1 minute through the jugular cannula; the cannula was flushed with 0.2 ml of heparinized saline (250 units/ml) to reduce the risk of clotting. The end of the infusion was designated as time zero (0). Blood samples (0.4 ml) were withdrawn from the cannula at various timepoints. The blood was immediately centrifuged to separate out the plasma. 100 µl of plasma was counted using a Packard Cobra Auto-Gamma to determine the concentration of NQ11/7.12 in the plasma.

Antibody buffering experiments. Samples were prepared for injection: 4.54 nmol anti-Ox antibody and 2.27 nmol Ox; 4.54 nmol D1.3 control antibody and 2.27 nmol Ox; or no antibody and 2.27 nmol Ox. Each sample was diluted to 1 ml with sterile PBS. The samples were warmed to 37° C., and then infused over 1 minute through the jugular vein cannula in Sprague-Dawley rats as described above. At various timepoints, 0.45 ml of blood was withdrawn and immediately centrifuged to separate out the plasma. 100 µl of plasma were counted directly by placing the plasma into 5 ml of Scintiverse II and counting in a Beckman LS6500 Scintillation Counter. 100 µl plasma was used in bound vs. free Ox experiments described below. For some rats, 0.1 ml of blood minus plasma was analyzed. These samples were first decolorized by incubating at 40° C. in 0.3 ml of Scintigest (Fisher Scientific):isopropanol (1:2 v/v) for one hour. Then 0.2 ml of 30% $H_2O_2$ was added dropwise, and the solution was incubated at room temperature for 15 minutes. Pipetting up and down was needed to break up some clumps. The solution was incubated at 40° C. before placing it into 5 ml of Scintiverse II. The samples were allowed to sit overnight before counting to reduce chemiluminescence. Control samples were prepared using known amounts of Ox to aid in analysis.

Separation of bound and free Ox using 187.1-Sepharose affinity resin. The rat anti-mouse kappa antibody 187.1 (see Example 1) was isolated from spent culture medium and purified by passage over a Protein A-Sepharose affinity column. Ten g of CNBr-activated Sepharose 4 Fast Flow (Amersham Biosciences) were washed and coupled with 187.1 according to manufacturer's protocol. Two mg 187.1 per 10 g of swelled resin were used.

During the antibody buffering experiments, 100 µl of plasma was loaded onto the 187.1 column immediately after centrifugation. Three ml of PBS followed by three ml of 0.2 M glycine (pH 2.5) were then applied onto the column as described in Example 1. All PBS fractions and all glycine fractions were collected separately for each timepoint and dried down in the SpeedVac. The residue was resuspended in 150 µl PBS and then transferred to a scintillation vial with 5 ml Scintiverse II for counting.

Long term buffering experiment. Samples of NQ11/7.12 and Ox were prepared and infused into Sprague-Dawley rats as described above. Blood samples (0.4 ml) were taken at time 1, 10, 20, 50, 90, and 120 minutes. 100 µl plasma were counted directly and 100 µl were placed on a 187.1 column to separate bound and free Ox. At 24 hours and again at 48 hours following the first administration, 2.27 nmol Ox in 0.5 ml PBS was infused over 1 minute through the jugular cannula. Timepoints were again taken and analyzed as above.

The effect of NQ11/7.12 on Ox lifetime in rat plasma. To determine its pharmacokinetic behavior, tritiated Ox was infused into a rat through a jugular cannula, and elimination of Ox was followed through blood sampling, separation of the plasma by centrifugation, and scintillation counting of the plasma. The concentration of Ox declined rapidly from the plasma with an elimination half-life of 1.2 minutes.

The affinities of three kineticaliy-characterized monoclonal antibodies that specifically bind Ox were determined at 37° C. using fluorescence spectroscopy and were 1.3 nM (NQ11/7.12), 46 nM (NQ16/113.8), and 42 nM (NQ22/16.4). An isotype-matched ($IgG_1$) anti-hen egg lysozyme antibody, D1.3, was used as a control. Each rat in these studies was used only once to limit the possibility of a rat anti-mouse antibody response. The pharmacokinetic parameters of Ox when administered with the different antibodies is presented in Table 1.

TABLE 1

Pharmacokinetic Parameters of Ox Buffered by Different Antibodies

| Antibody | Affinity for Ox | $t_{1/2}\alpha$ (min) | $t_{1/2}\beta$ (min) | C(0) (nM) | AUC (nmole-min/L) | Vd (ml) | CL (ml/min) |
|---|---|---|---|---|---|---|---|
| D1.3 | None | 1.2 | 9.9 | 25 | 253 | 112.5 | 9.0 |
| NQ11 | 1.34 nM | — | 19.7 | 84 | 2848 | 2.26 | 0.08 |
| NQ16 | 46 nM | 1.17 | 5.3 | 71.8 | 393 | 45.0 | 5.8 |
| NQ22 | 42 Nm | 1.36 | 6.1 | 58.8 | 406 | 49.1 | 5.6 |

Antibodies were attractive therapeutic vehicles, in part, because of their long plasma half-life, which is far longer than the pharmacokinetic lifetime of most drugs. The residence time in the plasma of the radioiodinated monoclonal antibody NQ11/7.12 was determined. The NQ11/7.12 antibody was infused into a rat, and the elimination of NQ11/7.12 was followed through blood sampling, separation of the plasma by centrifugation, and gamma counting of the plasma. The concentration of NQ11/7.12 declined slowly with an elimination half-life from the plasma of 20 hours. This lifetime was so long that the anti-Ox antibody concentration was effectively constant (200+/−30 nM) over the course of all the pharmacokinetic studies, except where noted.

Figure 6:
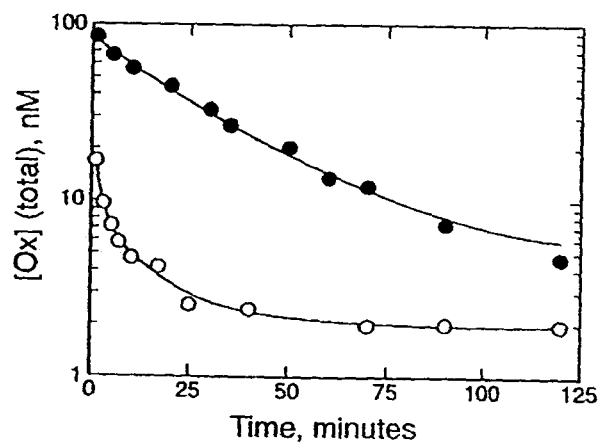
FIG. 6 illustrates elimination of Ox administered with a control antibody D1.3 (open circles, $t_{1/2}$=1.2 min) occurs more rapidly than when Ox is administered with the anti-Ox antibody NQ11/7.12 (filled circles, $t_{1/2}$=19.7 min). Ox was infused with each antibody to Sprague Dawley rats through a jugular vein cannula. Each point represents data collected from 5 animals.

Ox was administered with twice the molar amount of NQ11/7.12 or the control antibody through the rat's jugular cannula. As shown in FIG. 6, administration of Ox with NQ11/7.12 showed a significant prolongation of Ox residence time with an Ox elimination half-life of 20+/−2 minutes. Comparison of the two curves indicated that much of the Ox in the control was cleared from the plasma before the first timepoint could be sampled. The remaining Ox administered with D1.3 showed biphasic elimination kinetics; most was eliminated from the plasma with a half-life of 1.2+/−0.2 minutes, and a smaller amount had a half-life of 10+/−2 minutes. The seventeen-fold increase in half-life of Ox when administered with an anti-Ox antibody indicated that NQ11/7.12 binding was opposing Ox elimination from the plasma. As a control, analysis was also performed on the cellular fraction of the blood in order to determine if cells were a significant repository for the Ox. The Ox concentration in the cellular fraction ranged between 1-2% of the total Ox concentration in the plasma, which indicated that an insignificant amount of Ox was retained in this fraction. No adverse effects were noted in the animal subjects.

The effect of NQ11/7.12 on free Ox concentration. Bound and free forms of Ox in plasma fractions from the animals were separated on an affinity column. Samples resulting from D1.3 co-administration were processed in parallel, though no significant antibody-bound label was expected or found. An immobilized rat anti-mouse kappa antibody was used to trap antibody-Ox complexes while free Ox eluted from the column with a PBS wash (free Ox fraction).

Figure 7:
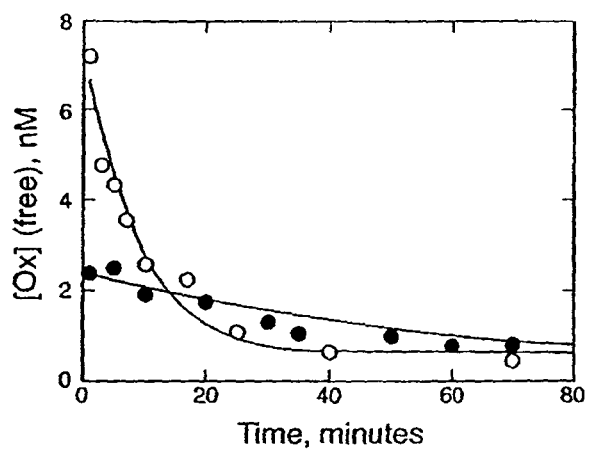
FIG. 7 presents the concentration of free Ox in the plasma of animals when Ox was administered with NQ11/7.12 (filled circles) versus D1.3 (open circles).

This analysis confirmed that a free pool of Ox existed in the rat plasma whether the Ox was administered with D1.3 or with NQ11/7.12 (FIG. 7). Initially, when Ox was administered alone or with D1.3 the amount of free Ox was high (6.8 nM), but it quickly decreased with an elimination half-life of 6.0+/−1 minutes. However, when Ox was administered with NQ11/7.12, the initial free concentration of Ox was low (2.2 nM). This low concentration remained fairly stable over time with an Ox elimination half-life of 41+/−6 minutes. Therefore, the presence of NQ11/7.12 appeared (according to non-limiting theory) to be buffering the free Ox according to the herein described equilibrium principle of antibody buffering of a ligand. The buffered free Ox concentration shown in FIG. 7 declined from 2.2 nM to 0.8 nM in the plasma over the span of an hour, whereas more than half of the unbuffered Ox was eliminated from the plasma before the first timepoint was sampled. The 2.2 nM and 0.8 nM endpoints bracket the $K_d$ of NQ11/7.12 (1.3 nM).

Figure 8A:
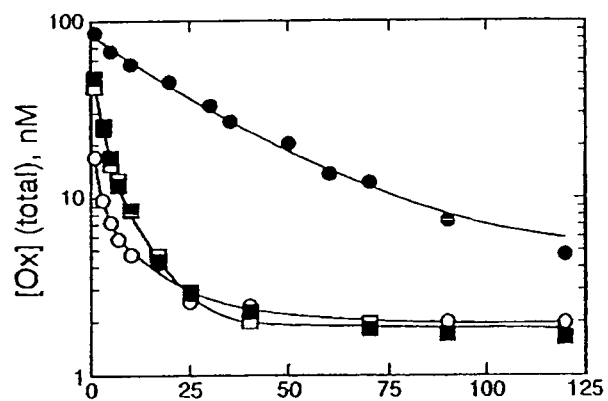
FIG. 8A: Total Ox vs. time. Antibodies NQ16/113.8 (filled squares) and NQ22/16.4 (open squares), which have higher $K_d$s than NQ11/7.12, were administered with Ox and compared with Ox administered with NQ11/7.12 (filled circles). Ox was also administered with the non-specific anti-lysozyme antibody D1.3 (open circles).

The effect of antibody $K_d$ on Ox lifetime in rat plasma. The correlation between antibody $K_d$ and the capability of an antibody to retard Ox elimination from the plasma was determined. For this experiment, three anti-Ox antibodies NQ11/7.12, NQ16/113.8, and NQ22/16.4, were used. NQ16/113.8, and NQ22/16.4 each had a similar $K_d$ for Ox, which was significantly higher than that of NQ11/7.12 (see Table 1). Ox was administered to rats with either NQ16/113.8 or NQ22/16.4. The total Ox concentration was measured through blood sampling (FIG. 8A). The concentration of Ox administered with NQ11/7.12 or with D1.3 is also shown in FIG. 8A for comparison. Both NQ16/113.8 and NQ22/16.4 retarded total Ox elimination from the plasma. This increase in Ox half-life did not approach the extent of the increase in Ox half-life when administered with NQ11/7.12, which had a much higher affinity for Ox. Therefore, antibody $K_d$ was related to the elimination rate of total Ox in the plasma.

Figure 8B:
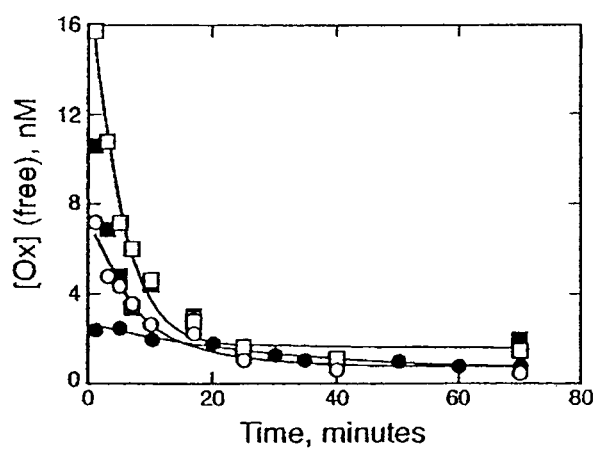
FIG. 8B. Free Ox vs. time. The concentration of free Ox in the plasma was also determined in animals that received Ox with NQ11/7.12 (filled circles); NQ16/113.8 (filled squares); NQ22/16.4 (open squares); or D1.3 (open circles).

In addition, antibody $K_d$ affected the free pool of Ox in the rat plasma as shown in FIG. 8B. Plasma was loaded onto the rat anti-mouse kappa antibody affinity column, and free and bound Ox fractions were eluted. Initially, the free concentration of Ox (between 10 and 16 nM) administered with NQ16/113.8 or NQ22/16.4 was higher than that of Ox (2.2 nM) administered with NQ11/7.12. This free concentration declined much more rapidly than the free Ox administered with NQ11/7.12. Thus, anti-Ox antibody $K_d$ determined the buffering capacity of the antibody.

Figure 9A:
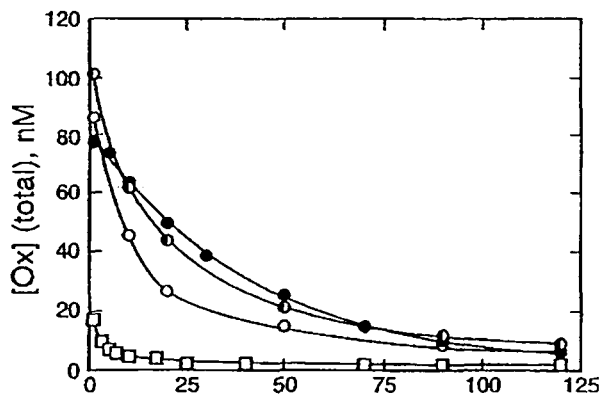
FIG. 9 shows plasma half-life of total Ox (FIG. 9A) and free Ox (FIG. 9B). Ox was co-administered to rats with NQ11/7.12 (filled circles) or administered alone 24 hours after NQ11/7.12 infusion (half-filled circles) or 48 hours after NQ11/7.12 infusion (open circles). Ox was also administered with a control D1.3 antibody (open squares).
Figure 9B:
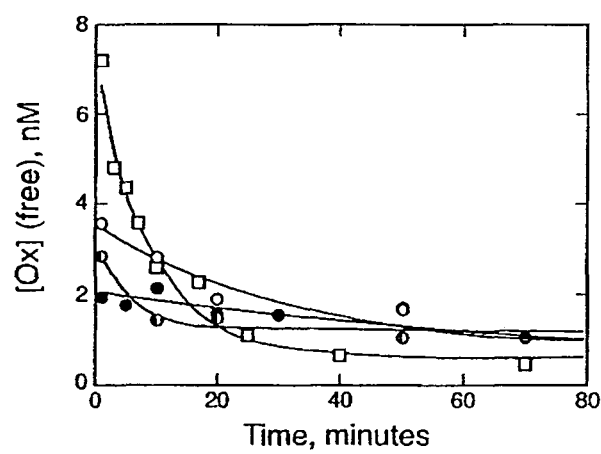

Long-term buffering of NQ11/7.12. Whether NQ11/7.12 retained its bility to buffer Ox concentration in the plasma days after the initial antibody infusion as determined. For these experiments, NQ11/7.12 was administered only once. Ox as initially co-administered with NQ11/7.12. Additional aliquots of Ox alone were administered at 24 hours and at 48 hours. Blood samples were obtained to follow total Ox elimination from the plasma. As shown in FIG. 9A, the Ox pharmacokinetic lifetime at 24 hours and 48 hours showed only small changes from the kinetics following the initial NQ11/7.12 administration, which could be attributed to the slow clearance in circulating antibody over time. Ox co-administered with the D1.3 control antibody is shown for comparison. Free vs. bound Ox separation was also performed on these plasma samples; the data are presented in FIG. 9B. Initially, the free Ox concentration at 24 hours and 48 hours was higher than when Ox was administered concurrently with the antibody buffer. However, the free concentration quickly normalized as Ox was bound by the NQ11/7.12 antibody already present in the plasma. This was an elimination pattern similar to the pattern observed when Ox and NQ11/7.12 were administered together. Therefore, an anti-Ox antibody buffered the concentration of free Ox in the plasma days after the initial antibody infusion. As shown in FIG. 9, whether the Ox was co-administered or re-administered at a later time, the equilibration of Ox and the antibody within the plasma was much more rapid than elimination of free Ox.

Example 3

Antibody Buffering of Lysozyme

Methods

Preparation $^{14}C$ lysozyme. Lysozyme was radioactively labeled with $^{14}C$ using reductive methylation, a procedure adapted from Habeeb (Habeeb, 1983). $^{14}C$ formaldehyde was obtained from New England Nuclear (specific activity 40-60 mCi/mmol). The glass ampoule was placed on dry ice to condense the formaldehyde gas. A labeling mix consisted of 0.7 pmol lysozyme (from a 20 mg/ml solution in phosphate buffer), 3.5 pmol NaCNBH$_3$ (from a 0.1 M NaCNBH$_3$ solution, freshly prepared), and 0.1 M phosphate buffer (NaH$_2$PO$_4$, pH 8.0 with NaOH) which was added to bring the total volume to 1 ml. The labeling mix was added to the ampoule and the reaction was allowed to proceed for 30 minutes, mixing every 8 minutes. To the ampoule 0.5 ml of 0.05 M borate buffer (H$_3$BO$_3$, pH 8.0) was added, and 1 µl aliquots were withdrawn for scintillation counting for quality control purposes. Then, the reaction mixture was dialyzed against 2×500 ml borate buffer, pH 7.0, followed by dialysis against 5×500 ml of sterile PBS. Aliquots of the dialysis buffer were added to scintillation fluid and counted to determine when dialysis was complete. SDS-PAGE was performed to assess protein purity, and the gel was subjected to autoradiography to verify that the $^{14}C$ tag was localized only to the lysozyme band. The protein concentration was determined by UV spectroscopy, using an extinction coefficient calculated from sequence (Perkins, 1986). One μl aliquots were withdrawn for scintillation counting to determine the specific activity of the lysozyme. The antibody solution was filter-sterilized and stored at 4° C. under $N_2$.

Anti-Lysozyme Antibody. The murine anti-lysozyme hybridoma, D1.3 (Amit et al., supra; Bhat et al., Nature 347: 483-85 (1990)), was grown in an oscillating bubble roller bottle (Pannell and Milstein, 1992). The resulting monoclonal antibody was purified from spent culture supernatant by passage over a lysozyme-Sepharose affinity column. Fractions were eluted with diethylamine (Fisher Scientific) into tubes containing 150 μl 1 M Tris, pH 7.4, and dialyzed against Protein A buffer (3M NaCl, 0.1 M glycine, pH 8.9). The dialysate was then passed over a Protein A-Sepharose CL-4B (Pharmacia) column. Fractions were eluted with a gradient of sodium citrate to citric acid and collected into tubes containing 100 μl 3M Tris, pH 8.8. The fractions were then dialyzed against PBS (25 mM $NaH_2PO_4$/125 mm NaCl, pH 7.0). SDS-PAGE was performed to verify purity. Protein concentration was determined by UV spectroscopy, using an extinction coefficient calculated from sequence (Perkins, 1986). The antibody solution was filter-sterilized and stored at 4° C. under $N_2$. The $K_d$ of D1.3 was 3.7 nM (at 20° C.) (Foote and Winter, supra).

An ELISA was performed with the D1.3 antibody to show that its ability to bind lysozyme was retained when using the $^{14}C$ conjugate. Wells in a 96-well plate were coated with 100 μg/ml lysozyme or $^{14}C$-lysozyme in a carbonate buffer (5.0 mM $NaHCO_3$, pH 9.6) and allowed to incubate at 37° C. for 1 hour. The plate was washed with PBS, blocked with a milk buffer, washed again with PBS, and then incubated for an hour with 20 ng/ml D1.3 in PBS with 10 mg/ml BSA added. Control wells were incubated with an antibody that did not bind lysozyme, NQ10/2.22. Following the incubation, the plate was again washed and incubated for one hour with the secondary antibody, peroxidase conjugated goat anti-mouse IgG, Fc fragment specific (Jackson ImmunoChemicals, West Grove, Pa.). The plate was read with a kinetic microplate reader (Molecular Devices Corp., Sunnyvale, Calif.) after adding color mix (1 mM ATBS substrate and 4 mM $H_2O_2$ in a 50 mM sodium citrate/50 mM citric acid buffer).

Antibody buffering experiments. Rats (300 g Sprague-Dawley males, Zivic Laboratories, Zelionople, Pa.) were implanted with a jugular vein cannula. The rats were freely moving throughout the experiment and were allowed access to food and water. Samples were prepared for infusion consisting of 43 μg $^{14}C$-lysozyme with or without 450 μg D1.3 antibody. The volume was brought to 1 ml using sterile normal saline and the sample was incubated at 37° C. prior to use. The sample was infused through the jugular cannula over 5 minutes using an HP infusion pump. Following the infusion, the cannula was flushed with 0.2 ml of heparinized saline (250 units/ml) to reduce the risk of clotting. The end of the infusion was designated as time zero (0). Blood samples (0.5 ml) were withdrawn from the cannula at various timepoints. The blood was immediately centrifuged to separate out the plasma. Plasma (0.1 ml) was mixed with 5 ml scintillation fluid and counted. Another 0.1 ml was used in bound vs. free lysozyme experiments described herein. The cellular pellet was mixed with scintillation fluid and counted also.

Separation of free and bound lysozyme. Following blood sample centrifugation to separate out the plasma, 0.1 ml of plasma was loaded onto a 1.5 ml Protein A-Sepharose minicolumn. The column was washed with 3 ml of PBS in 0.5 ml increments followed by 3 ml of 100 mM citric acid in 0.5 ml increments. The PBS (free lysozyme) and citric acid (antibody-bound lysozyme) fractions were collected separately for each timepoint. TCA precipitation was performed on the fractions. The protein precipitate was washed with acetone and the precipitate redissolved in PBS (although not all of the precipitate dissolved). The liquid and remaining pellet were transferred into 4 ml scintillation fluid for counting.

Antibody Buffering with Varied Amounts of Antibody. Sprague-Dawley rats implanted with a jugular cannula were infused with 43 μg $^{14}C$-lysozyme and either 450 μg or 900 μg of D1.3 antibody. The volume infused was brought up to 1 ml using sterile normal saline. The samples were prepared and infused and timepoints were taken and analyzed as described above. Bound vs. free separation analyses were not performed.

Antibody Buffering with Varied Amounts of Lysozyme. Sprague-Dawley rats implanted with a jugular cannula were infused with 450 μg of D1.3 antibody and either 43 μg or 430 μg of $^{14}C$-lysozyme. The samples were prepared, infused, and timepoints were taken and analyzed as described above.

Double Infusion Experiment. Two samples were prepared for infusion. The first sample, consisting of 450 μg D1.3 antibody diluted to 0.5 ml with sterile normal saline, was infused over 4 minutes using an HP infusion pump. The rat was allowed to move freely in its cage for 10 minutes to allow the antibody time to equilibrate within the circulation. Then the second sample, consisting of 43 μg $^{14}C$-lysozyme made up to 0.5 ml using sterile normal saline, was infused over 4 minutes. The end of the second infusion was designated as time zero (0). Blood samples were taken and analyzed as described above.

Figure 10A:
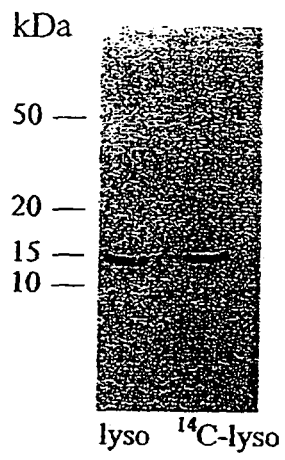
FIG. 10A presents an SDS-PAGE analysis of unlabeled lysozyme (lyso) and $^{14}$C-lysozyme ($^{14}$C-lyso).
Figure 10B:
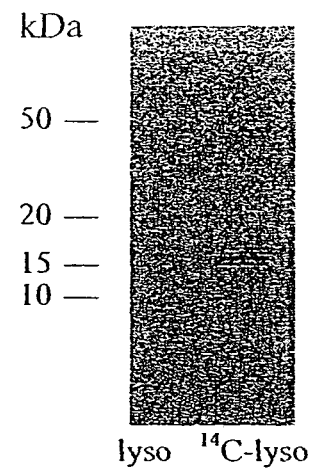
FIG. 10B presents an autoradiographic analysis of the SDS-PAGE gel.
Figure 10C:
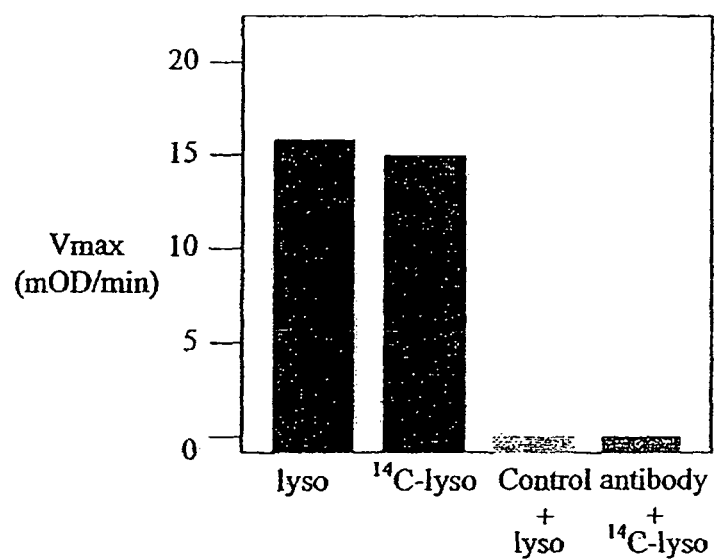
FIG. 10C provides the results from an ELISA determining the binding of the anti-lysozyme antibody D1.3 to lysozyme (lyso) and $^{14}$C-lysozyme ($^{14}$C-Lyso) and the binding of a non-specific antibody (NQ10/2.22) to lysozyme (control antibody+lyso) and $^{14}$C-lysozyme (control antibody+$^{14}$C-lyso).

$^{14}C$-lysozyme. In previous studies of lysozyme pharmacokinetics in the rat, the amount of lysozyme in the plasma was quantified by an enzymatic assay (Franssen et al., Pharm. Res. 8:1223-30 (1991)). However, D1.3 blocked the enzymatic activity of lysozyme; therefore, lysozyme was radiolabeled with $^{14}C$ so that its amount in plasma samples could be measured. Reductive methylation of lysozyme with $^{14}C$-formaldehyde yielded a $^{14}C$-lysozyme conjugate with a specific activity of $7.4 \times 10^7$ cpm/mg. Thus, the lysozyme was sufficiently labeled to be detected above background level in the rat plasma. As shown in FIG. 10, the purity of the $^{14}C$-lysozyme was determined using SDS-PAGE (FIG. 10A), and the radioactive signal that localized to the lysozyme band was shown using autoradiography (FIG. 10B). The ability of D1.3 to bind the $^{14}C$-lysozyme conjugate effectively was determined by ELISA (FIG. 10C). D1.3 lysozyme binding was retained with the $^{14}C$ conjugate.

Figure 11:
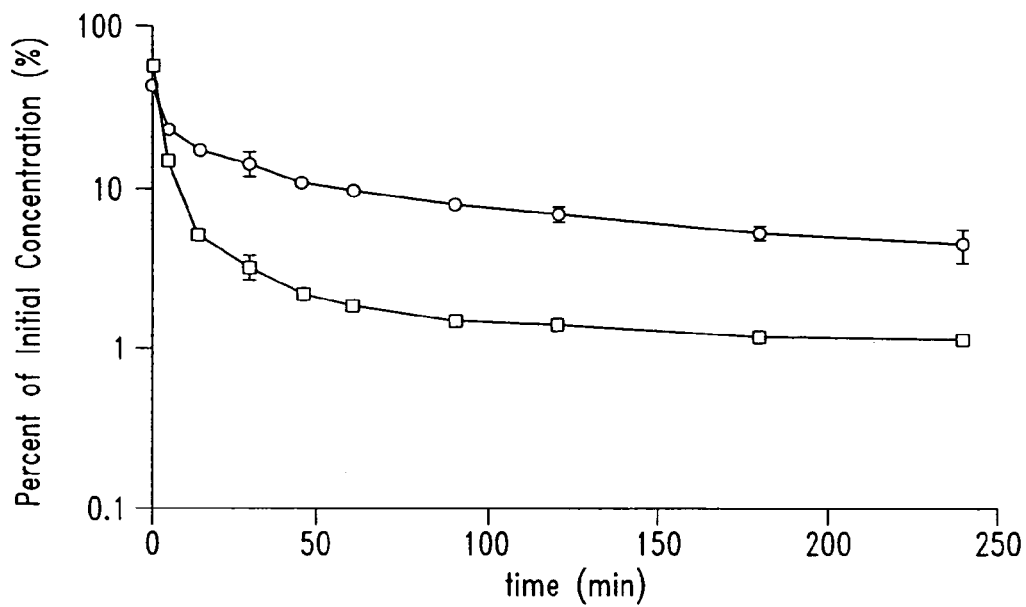
FIG. 11 presents the pharmacokinetics in plasma of lysozyme in the presence and absence of an anti-lysozyme antibody. $^{14}$C-lysozyme was administered to rats alone (squares) or with the anti-lysozyme antibody D1.3 (circles).

Pharmacokinetics of Lysozyme in Rat Plasma. To determine the pharmacokinetic profile of lysozyme using a radioactive method of lysozyme detection, $^{14}C$-lysozyme was infused through a jugular cannula into the bloodstream of a rat. Lysozyme elimination was followed through blood sampling at various time intervals spanning 4 hours. The plasma was collected after centrifugation and subjected to scintillation counting. Lysozyme was found to have a plasma β-half life of 16.4 minutes (FIG. 11). Each rat in these and in the following studies was used only once to limit the possibility of an immune response to either the lysozyme or the antibody.

Pharmacokinetics of Antibody-buffered Lysozyme. The murine anti-lysozyme antibody D1.3 was used as an antibody buffer for $^{14}C$-lysozyme, according to the herein described equilibrium principle of antibody buffering of a ligand. Lysozyme was administered with an equimolar amount of D1.3 through a rat's jugular cannula. As shown in FIG. 11, the concentration of lysozyme administered alone declined rapidly with an elimination half-life of 16.4 minutes. Administration of D1.3 with lysozyme significantly prolonged the residence time of lysozyme in the rat plasma, extending the β-half life to 42.8 minutes. Although the initial concentration of lysozyme appeared higher when it was administered on its own, that amount fell rapidly compared to lysozyme buffered by D1.3, indicating that D1.3 complexation indeed decreased the elimination rate.

Following plasma separation, the cellular pellet was counted in both this and the previous study (supra). Little radioactivity was found in this fraction, indicating that the cellular pellet was not a significant repository for lysozyme or lysozyme-antibody complexes.

Pharmacokinetics of Free Lysozyme. Following centrifugation to separate out the plasma for scintillation counting to determine the total lysozyme concentration, an aliquot of plasma was applied to a Protein-A Sepharose mini-column to separate bound and free forms of lysozyme. Free lysozyme was eluted with a PBS wash while lysozyme that was specifically bound to D1.3 was eluted with citric acid. The resulting large volumes of eluate precluded direct scintillation counting so TCA precipitation was performed to separate out the proteins. The resulting protein pellet was resistant to redissolving despite attempts with tissue solubilizers and other reagents; therefore, the exact free lysozyme concentration was difficult to ascertain. Nevertheless, analysis of the level of lysozyme alone and the level of lysozyme-D1.3 eluates prepared identically indicated a difference in the free lysozyme levels in these samples.

Figure 12:
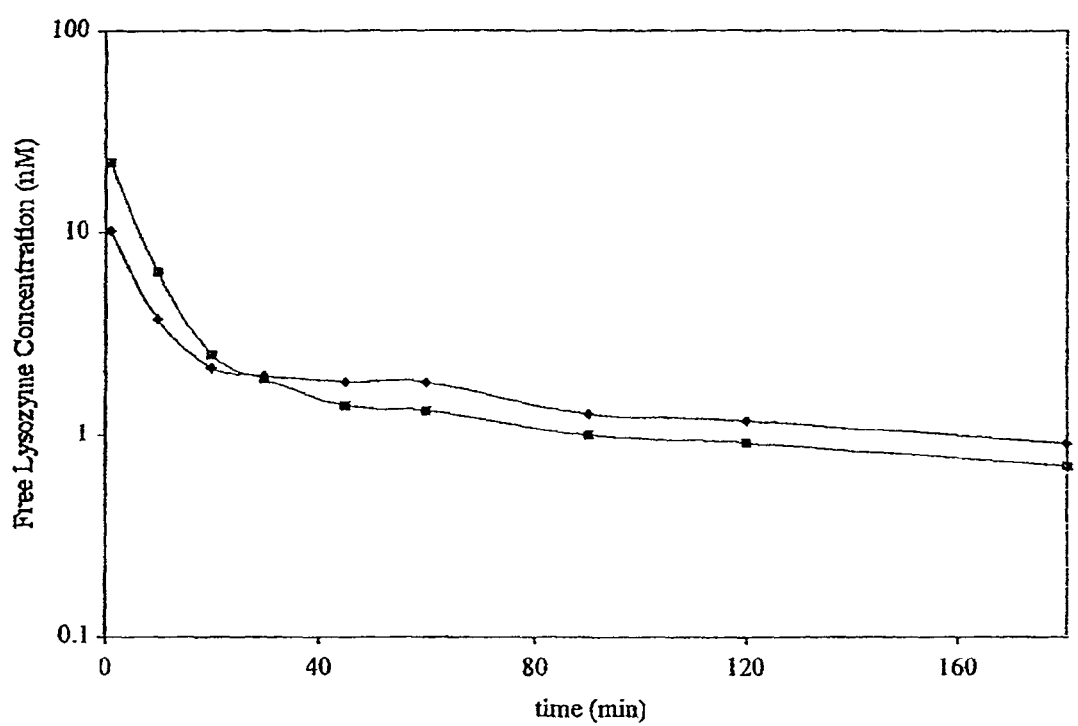
FIG. 12 shows the concentration in plasma of free $^{14}$C-lysozyme when $^{14}$C-lysozyme was administered to rats with anti-lysozyme antibody D1.3 (diamonds) and when $^{14}$C-lysozyme was administered alone (squares).

If the D1.3 antibody acted as a buffer for its cognate ligand, lysozyme, the antibody acted as a reservoir of that ligand, maintaining the free lysozyme concentration at a fairly constant level. As shown in FIG. 12, a free pool of lysozyme existed when lysozyme was administered with D1.3, and this free pool remained at a more constant level during the course of the experiment than the level of free lysozyme observed when lysozyme was administered alone (FIG. 12). Therefore, the presence of D1.3 appeared to provide an antibody buffering effect according to the herein described equilibrium principle of antibody buffering of a ligand.

Figure 13:
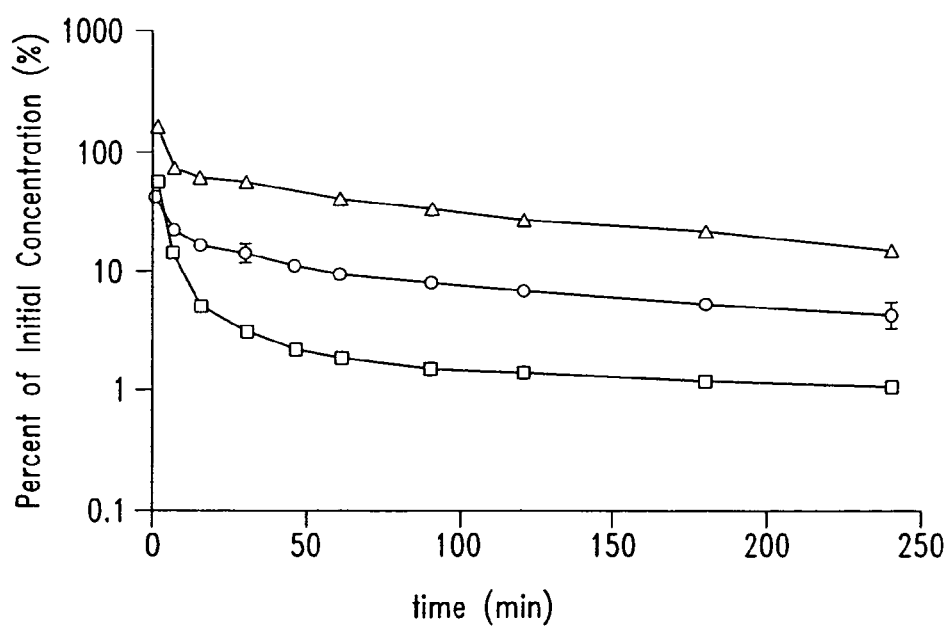
FIG. 13 illustrates the effect on the half-life of lysozyme administered systemically with increasing concentrations of specific antibody. To groups of rats, $^{14}$C-lysozyme was administered without antibody (squares), with an equimolar concentration of D1.3 (circles), and with D1.3 at twice the molar concentration of lysozyme (diamonds).

The Effect of Varying Lysozyme and Antibody Concentration on the Buffering Capacity of D1.3. To determine the effect of various antibody concentrations on the buffering of total lysozyme in the rat plasma, $^{14}$C-lysozyme was administered with either equimolar or two times the molar amount of D1.3 into the rat plasma. Blood was sampled at various timepoints over the course of four hours. Plasma was again separated by centrifugation, and total lysozyme concentration was determined via scintillation counting. As presented in FIG. 13, administration of lysozyme with two times the molar amount of D1.3 prolonged the β-half life of lysozyme to 61.3 minutes. This half-life was significantly different than the β-half life of lysozyme when lysozyme was administered with equimolar D1.3 (β-half life of 42.8 minutes). Therefore, addition of more antibody to the buffer system appeared to prolong ligand half-life to a greater extent.

Figure 14:
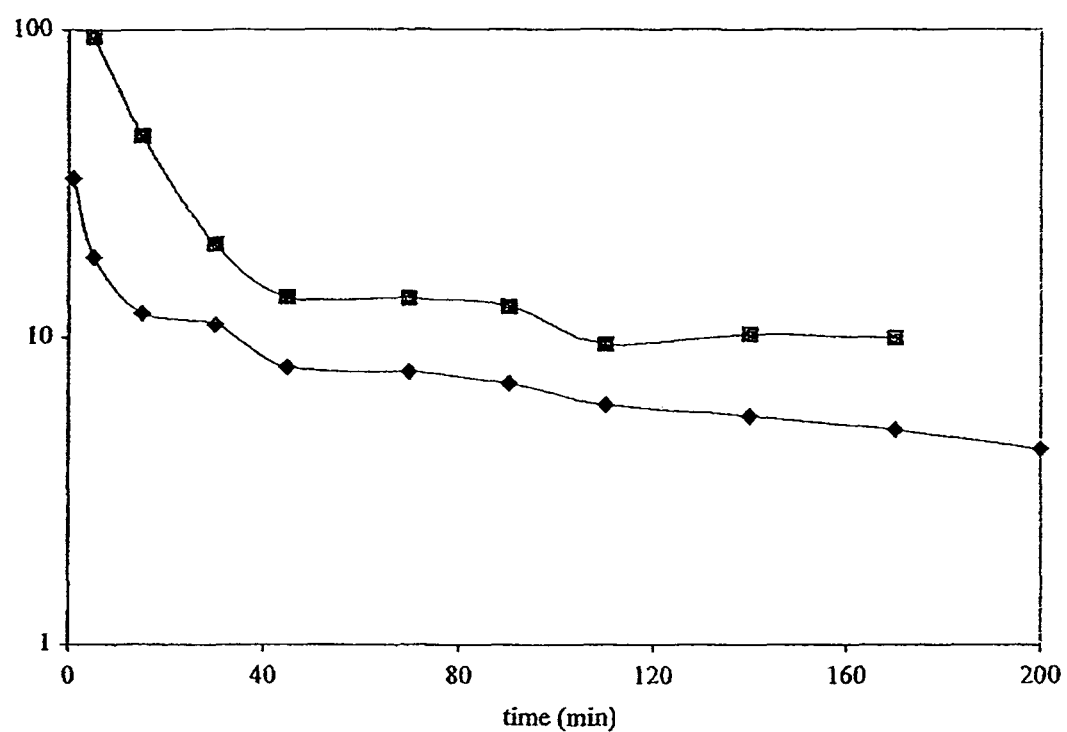
FIG. 14 presents the effect on the half-life of lysozyme administered systemically when increasing concentrations of lysozyme are administered to animals in the presence of an anti-lysozyme antibody. The anti-lysozyme antibody D1.3 was administered with an equimolar amount of $^{14}$C-lysozyme (diamonds). D1.3 was also administered with $^{14}$C-lysozyme at a concentration 10-fold the molar amount of D1.3 (squares).

Experiments were also performed to determine the effect of increasing the lysozyme concentration on the total lysozyme concentration over time in the rat plasma. D1.3 was infused into the jugular cannula of the rat with either equimolar or ten times the molar concentration of $^{14}$C-lysozyme. Timepoints were taken and plasma analyzed for total lysozyme concentration as described above. Although the initial lysozyme concentration in the rats given ten times as much lysozyme was much higher than that of the equimolar lysozyme concentration rats, it rapidly plummeted to a level about twice as high as that of the rats given the lower lysozyme concentration (FIG. 14). This observation indicated that while significantly increasing the amount of ligand had a large effect on the initial total lysozyme concentration, it yielded only a modest increase in the ligand amount at later timepoints.

Figure 15:
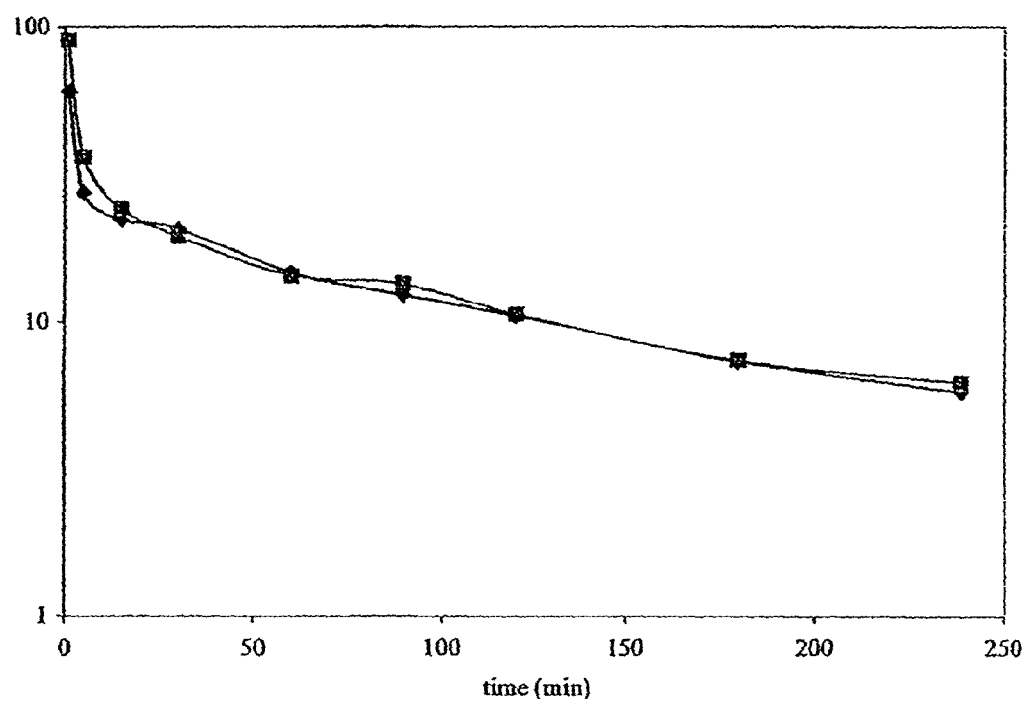
FIG. 15 illustrates the elimination of lysozyme in plasma when lysozyme is administered concurrently or sequentially with the anti-lysozyme antibody D1.3. One group of rats was initially infused with D1.3 only followed ten minutes later by administration of $^{14}$C-lysozyme (squares). Another group of animals was infused concurrently with D1.3 and $^{14}$C-lysozyme (diamonds).

Lysozyme administered following D1.3 equilibration within the plasma. An additional experiment was performed in which D1.3 was infused alone into the rat plasma. Ten minutes following this infusion, to allow for equilibration of the antibody within the plasma, an equimolar amount of lysozyme was administered through the jugular cannula of the rat. The resulting pharmacokinetics were followed through blood sampling as described above. As shown in FIG. 15, the initial concentration of lysozyme was high, but it quickly equilibrated to a level very similar to that attained when the D1.3 and lysozyme were administered together. This indicated that D1.3 was retained well in the circulation, and that its ability to bind lysozyme effectively was not altered in vivo.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An antibody buffering method for maintaining a desired concentration range of a soluble small molecule or polypeptide ligand in a subject, comprising:
   (a) isolating one or a plurality of antibodies, or an antigen-binding fragment thereof, that has been generated in vivo or in vitro and that specifically binds to a small molecule or polypeptide ligand in solution;
   (b) determining, for each of the antibodies or antigen-binding fragments thereof of (a), an antibody dissociation constant, $K_D$, for binding to the ligand;
   (c) selecting, from among the antibodies or antigen-binding fragments thereof of (a), an antibody or an antigen-binding fragment thereof that has said antibody dissociation constant, $K_D$, having a value as determined in (b) that is within tenfold of the desired concentration range of the ligand; and
   (d) administering to the subject simultaneously or sequentially and in either order at least one dose of said ligand and said antibody, or antigen-binding fragment thereof, selected in step (c), to attain the desired concentration range of the ligand as unbound free ligand in the subject, wherein the antibody-to-ligand ratio is 1:1 or at least 2:1; whereby antibody buffering delays clearance of the ligand as a result of equilibrium distribution between (i) the ligand complexed to the antibody or antigen-binding fragment thereof and (ii) the unbound free ligand, such that the half-life of the ligand when administered with the antibody or antigen-binding fragment thereof is increased by at least two-fold relative to the half-life of the ligand when administered alone.

2. An antibody buffering method for maintaining a desired concentration range of a soluble small molecule or polypeptide ligand in a body compartment in a subject, comprising:
   (a) isolating one or a plurality of antibodies, or an antigen-binding fragment thereof, that has been generated in vivo or in vitro and that specifically binds to a small molecule or polypeptide ligand in solution;

(b) determining, for each of the antibodies or antigen-binding fragments thereof of (a), an antibody dissociation constant, $K_D$, for binding to the ligand:, (c) selecting, from among the antibodies or antigen-binding fragments thereof of (a), an antibody or an antigen-binding fragment thereof that has said antibody dissociation constant, $K_D$, having a value as determined in (b) that is within tenfold of the desired concentration range of the ligand; and (d) administering to the subject simultaneously or sequentially and in either order at least one dose of said ligand and said antibody, or antigen-binding fragment thereof, selected in step (c), to attain the desired concentration range of the ligand as unbound free ligand in the subject, wherein the antibody-to-ligand molar ratio is approximately 1:1 or at least 2:1;

whereby antibody buffering delays clearance of the ligand as a result of equilibrium distribution between (i) the ligand complexed to the antibody or antigen-binding fragment thereof and (ii) the unbound free ligand, such that the half-life of the ligand when administered with the antibody or antigen-binding fragment thereof is increased by at least two-fold relative to the half-life of the ligand when administered alone.

3. The method of claim 2, wherein the body compartment is selected from the group consisting of a central nervous system compartment, a pericardium, a pleural space, a retroorbital compartment, an eye compartment, a joint capsule, a lymphoid compartment, a peritoneal compartment, an intranasal compartment, a lung compartment, and a genitourinary compartment.

4. The method of claim 2, wherein the body compartment comprises a central nervous system compartment.

5. The method of claim 2, wherein the body compartment comprises a central nervous system compartment and the step of administering comprises introduction of the ligand intrathecally, intraventricularly, parenchymally, subdurally, subarachnoidally or epidurally.

6. The method of claim 2 comprising administering at least two doses of the ligand.

7. The method of claim 2, wherein the antibody is a monoclonal antibody.

8. The method of claim 2, wherein the antibody is a chimeric antibody or a humanized antibody.

9. The method of claim 2, wherein the antigen-binding fragment is selected from the group consisting of a Fab fragment, a Fab' fragment, a (Fab')2 fragment, an Fd fragment, an Fv fragment, an scFv, a dAb and a diabody.

10. The antibody buffering method according to claim 2 in which the concentration range is maintained in the body compartment for each of a first ligand and a second ligand, wherein steps (a)-(c) are performed for each of (i) a first antibody or plurality of antibodies, or an antigen-binding fragment thereof, that specifically binds to the first ligand and (ii) a second antibody or plurality of antibodies, or an antigen-binding fragment thereof, that specifically binds to the second ligand, and wherein the step (d) of administering comprises:

(1) administering to the body compartment simultaneously or sequentially and in either order at least one dose of the first ligand and the first antibody, or an antigen-binding fragment thereof, selected in step (c); and (2) administering to the body compartment simultaneously or sequentially and in either order at least one dose of the second ligand and the second antibody, or an antigen-binding fragment thereof, selected in step (c).

11. The method according to claim 2, wherein the one or a plurality of antibodies of step (a) comprises a plurality of antibodies, wherein in step (c) two or more antibodies are selected, each of said two or more antibodies having an antibody dissociation constant, $K_D$, for binding to the ligand as determined in (b) that has a value that is within tenfold of the desired concentration range of the ligand, and wherein step (d) comprises administering to the body compartment simultaneously or sequentially and in any order at least one dose of the first ligand and each of said two or more antibodies, or antigen-binding fragments thereof.

12. An antibody buffering method for maintaining a desired concentration range of a soluble small molecule or polypeptide ligand in a central nervous system compartment in a subject, comprising:

(a) isolating one or a plurality of antibodies, or an antigen-binding fragment thereof, that has been generated in vivo or in vitro and that specifically binds to a small molecule or polypeptide ligand in solution;

(b) determining, for each of the antibodies or antigen-binding fragments thereof of (a), an antibody dissociation constant, $K_D$, for binding to the ligand;

(c) selecting, from among the antibodies or antigen-binding fragments thereof of (a), an antibody or antibody-binding fragment thereof that has said antibody dissociation constant, $K_D$, having a value as determined in (b) that is within tenfold of the desired concentration range of the ligand; and (d) administering to the central nervous system compartment simultaneously or sequentially and in either order at least one dose of said ligand and said antibody, or antigen-binding fragment thereof, selected in step (c), to attain the desired concentration range of the ligand as unbound free ligand in the central nervous system compartment, wherein the antibody-to-ligand molar ratio is approximately 1:1 or at least 2:1;

whereby antibody buffering delays clearance of the ligand as a result of equilibrium distribution between (i) the ligand complexed to the antibody or antigen-binding fragment thereof and (ii) the unbound free ligand, such that the half-life of the ligand when administered with the antibody or antigen-binding fragment thereof is increased by at least two-fold relative to the half-life of the ligand when administered alone.

13. The method of claim 12, wherein the subject has a central nervous system disease or disorder that is selected from the group consisting of a neoplastic condition, a neurodegenerative disease, a vascular disease, and an autoimmune disease, and wherein the ligand is indicated for treating the central nervous system disease or disorder.

14. The method of claim 12, wherein the subject has a neoplastic condition of the central nervous system, and wherein the ligand is indicated for treating said condition.

15. The method of claim 14, wherein the neoplastic condition is selected from the group consisting of glioma, astrocytoma, neurofibroma, neuroblastoma, lymphoma, a brain metastasis, and a tumor that is present in at least one of brain parenchyma, meninges, cranial nerve, pituitary gland, pineal gland, oligodendroglia, ependyma and choroid plexus.

16. The method according to claim 12, wherein the antibody is a humanized antibody.

17. The method according to claim 12, wherein the antigen-binding fragment is selected from the group consisting of a Fab fragment, a Fab' fragment, a (Fab')2 fragment, an Fd fragment, an Fv fragment, an scFv, a dAb and a diabody.

18. The antibody buffering method according to claim 12 in which the concentration range is maintained in the central nervous system compartment for each of a first ligand and a second ligand, wherein steps (a)-(c) are performed for each of (i) a first antibody or plurality of antibodies, or an antigen-binding fragment thereof, that specifically binds to the first ligand and (ii) a second antibody or plurality of antibodies, or an antigen-binding fragment thereof, that specifically binds to the second ligand, and wherein the step (d) of administering comprises, simultaneously or sequentially and in either order:

(1) administering at least one dose of the first ligand and the first antibody, or an antigen-binding fragment thereof, selected in step (c); and (2) administering at least one dose of the second ligand and the second antibody, or an antigen-binding fragment thereof, selected in step (c).

19. The method according to claim 12, wherein the one or a plurality of antibodies of step (a) comprises a plurality of antibodies, wherein in step (c) two or more antibodies are identified, each of said two or more antibodies having an antibody dissociation constant, $K_D$, for binding to the ligand as determined in (b) that has a value that is within tenfold of said therapeutically effective concentration range of the ligand, and wherein step (d) comprises administering to the central nervous system compartment simultaneously or sequentially and in any order at least one dose of the first ligand and each of said two or more antibodies, or antigen-binding fragments thereof.

20. An antibody buffering method for maintaining a concentration range of a soluble small molecule or polypeptide ligand indicated for a particular disease or disorder in a subject or in a body compartment of a subject, comprising:

(a) isolating one or a plurality of antibodies, or an antigen-binding fragment thereof, that has been generated in vivo or in vitro and that specifically binds to a small molecule or polypeptide ligand in solution, said ligand having a concentration range indicated for a particular disease or-disorder in the subject or in a body compartment in the subject;

(b) determining, for each of the antibodies or antigen-binding fragments thereof of (a), an antibody dissociation constant, $K_D$, for binding to the ligand;

(c) selecting, from among the antibodies or antigen-binding fragments thereof of (a), an antibody or an antigen-binding fragment thereof that has said antibody dissociation constant, $K_D$, having a value as determined in (b) that is within tenfold of said concentration range of the ligand; and (d) administering to the subject, or to the body compartment in the subject, simultaneously or sequentially and in either order at least one dose of said ligand and said antibody, or antigen-binding fragment thereof, selected in step (c), to attain the concentration range of the ligand as unbound free ligand in the subject or in the body compartment, wherein the antibody-to-ligand molar ratio is approximately 1:1 or at least 2:1;

whereby antibody buffering delays clearance of the ligand as a result of equilibrium distribution between (i) the ligand-complexed to the antibody or antigen-binding fragment thereof and (ii) the unbound free ligand, such that the half-life of the ligand when administered with the antibody or antigen-binding fragment thereof is increased by at least two-fold relative to the half-life of the ligand when administered alone, thereby maintaining the concentration range, for the particular disease, disorder or indication, of the ligand in the subject or in the body compartment.

21. The method according to any one of claims 1, 2, 11, 12, 19, and 20, wherein the selecting step comprises selecting an antibody or antigen-binding fragment thereof that has said dissociation constant, $K_D$, having a value that is within three-fold of the desired concentration range of the ligand.

* * * * *